United States Patent [19]
Porrazzo et al.

[11] Patent Number: 5,837,197
[45] Date of Patent: Nov. 17, 1998

[54] POSITIVE FERTILITY TESTING AND REPRODUCTIVE HEALTH SYSTEM

[75] Inventors: Karen Pamela Orell Porrazzo; Edward Michael Porrazzo, both of Carmichael, Calif.

[73] Assignee: Personal Fertility Technologies, Inc., Gold River, Calif.

[21] Appl. No.: 577,334

[22] Filed: Dec. 22, 1995

[51] Int. Cl.⁶ .................................................. G01N 21/84
[52] U.S. Cl. ........................... 422/61; 435/305.2; 436/65; 436/809; 436/814; 436/906
[58] Field of Search ................................ 422/61; 436/65, 436/808–809, 814, 906; 435/305.2, 305.3, 288.4; 359/398, 396

[56] References Cited

U.S. PATENT DOCUMENTS

| | | | |
|---|---|---|---|
| 5,572,370 | 11/1996 | Cho | 436/63 |
| 5,639,424 | 6/1997 | Rausnitz | 422/61 |

OTHER PUBLICATIONS

BIOSIS 81:228419, 1996.

BIOSIS 95:163930, 1996.

*Primary Examiner*—Lyle A. Alexander
*Attorney, Agent, or Firm*—Theodore J. Bielen, Jr.

[57] ABSTRACT

This Invention relates to a fertility analysis and reproductive health system that is applicable to both female and male mammals. In particular the Invention is a portable, handheld, integrated unit which can be manufactured out of plastic. The unit can be disposable for hygienic purposes, or cleaned or sterilized for repeated use as desired. The present Invention has numerous aspects. These aspects include: (1) A unique, immediate testing methodology employing any and all female fluids or secretions called Positive Fertility Testing, "PFT"; (2) The creation of a plastic, completely integrated, portable, self-contained and self-focusing Examination System which relies on a visual reference system making it language independent; (3) A Test Area Section with replaceable slides where different, specific wavelengths of light are employed; (4) The embodiment of compound test areas so that multiple Positive Fertility Tests may be conducted simultaneously; (5) Implementing the ability to immediately perform two or more Positive Fertility Tests simultaneously using different female fluids or secretions; (6) Providing a novel battery powered microprocessor system to automatically perform the Positive Fertility Testing; (7) The embodiment of the most accurate indicator of positive ovulation whereby the woman may pinpoint times of greatest fertility, thereby knowing the optimum time period for achieving pregnancy. Alternatively, the use of the Invention as a birth control device; or to identify hormonal imbalances, irregular cycles or infertility; introduce young women to their fertility cycle, sexuality and health; (8) The embodiment of a unique, immediate testing methodology employing male fluids and secretions, including saliva, semen and sperm for determining the reproductive health and fertility status of a male called Positive Male Fertility Testing, "PMFT".

12 Claims, 8 Drawing Sheets

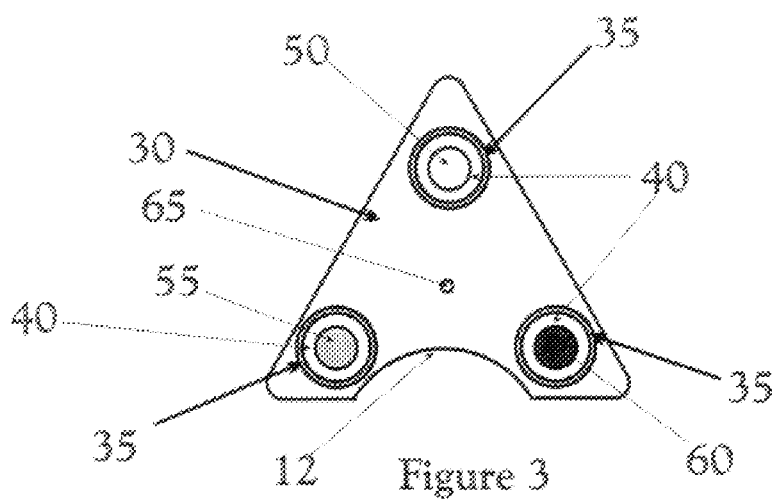
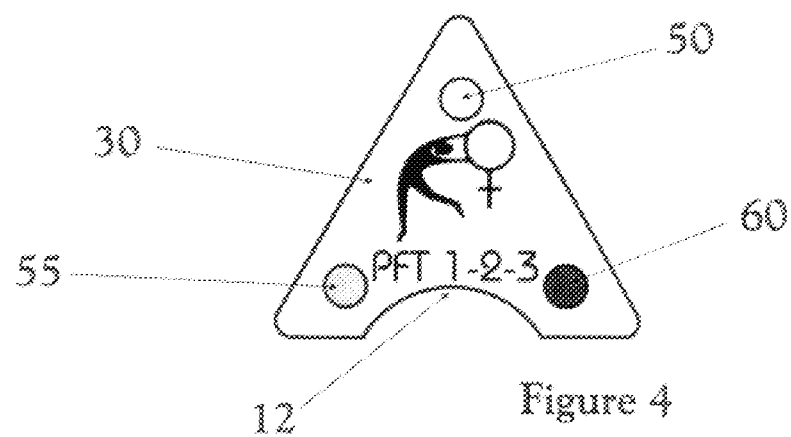

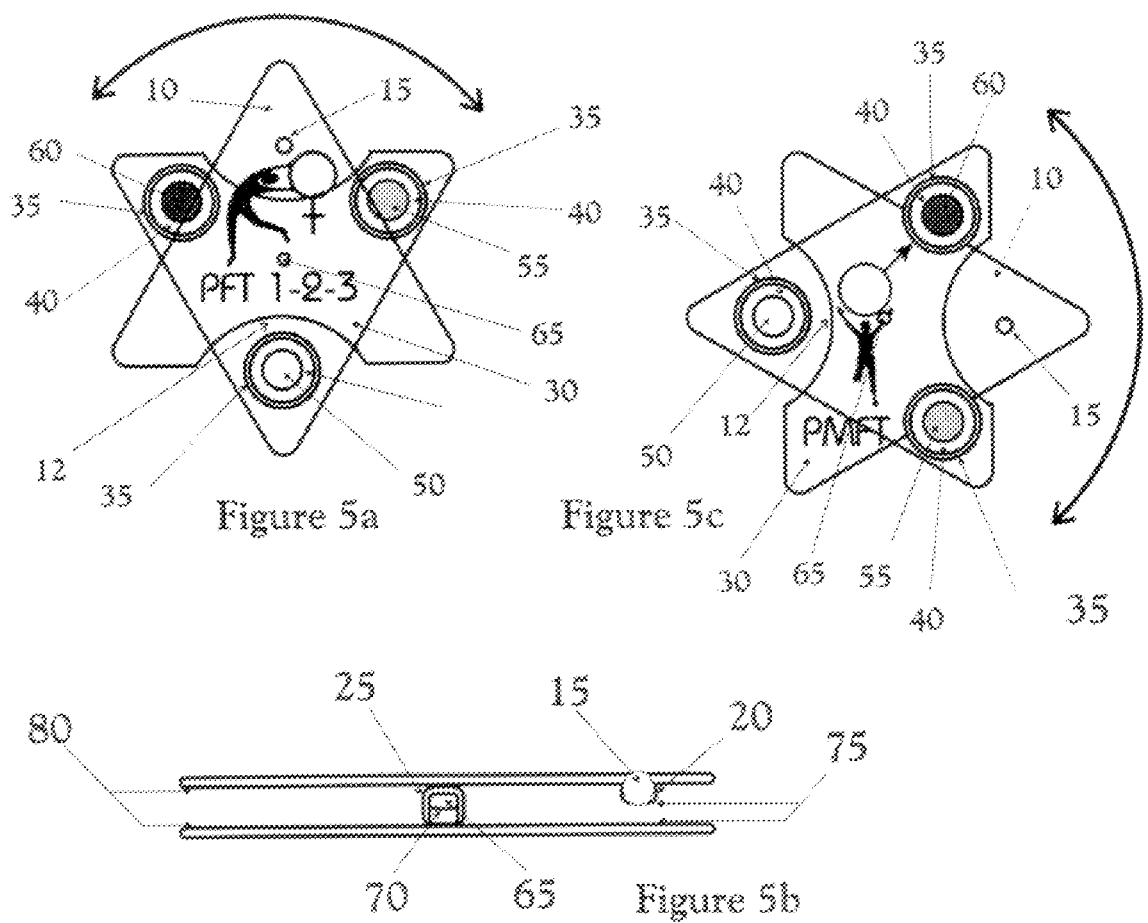

Figure 6a
Figure 6b
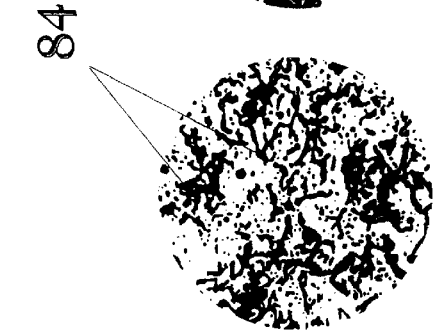
Figure 6c
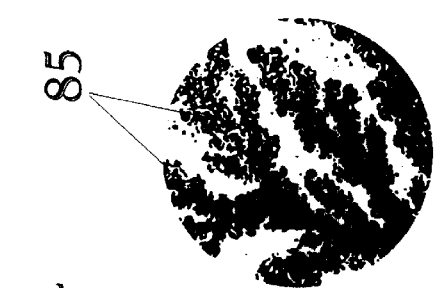
Figure 6d
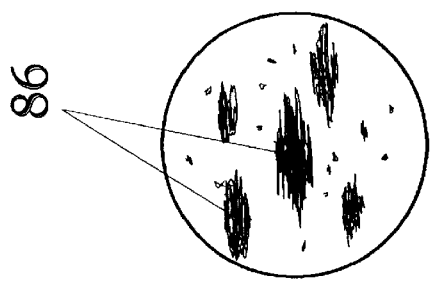
Figure 6e
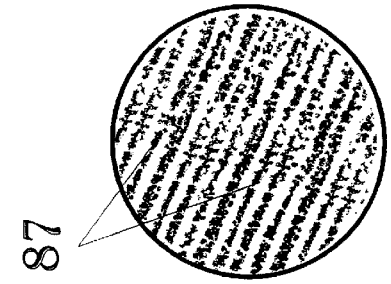
Figure 6f
Figure 6g
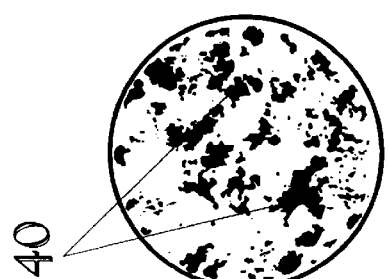
Figure 6h
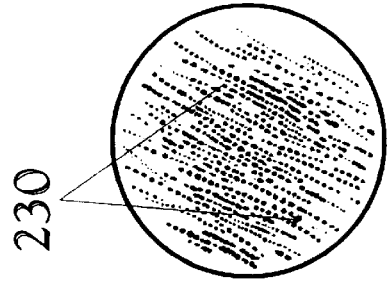
Figure 6i
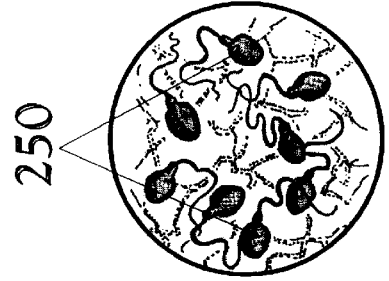
Figure 6j

| PFT 1-2-3 | 🐦 | ::: | /// | ☽ | Cervical Mucous | | | | | 🐦 | ::: | /// | ☽ | Cervical Mucous |
|---|---|---|---|---|---|---|---|---|---|---|---|---|---|---|
| Day/Date | Example | | | | | Day/Date | | | | | | | | |
| ♡ Mon/3-4-96 | | ✓ | | | Dry | Mon/ | | | | | | | | |
| Tue/3-5-96 | | | ✓ | | Pasty | Tue/ | | | | | | | | |
| ♡ Wed/3-6-96 | | | ✓ | | Creamy | Wed/ | | | | | | | | |
| Thr/3-7-96 | ✓ | | | | Slippery | Thr/ | | | | | | | | |
| Fri/3-8-96 | ✓ | | | | Slippery | Fri/ | | | | | | | | |
| Mon/ | | | | | | Mon/ | | | | | | | | |
| Tue/ | | | | | | Tue/ | | | | | | | | |
| Wed/ | | | | | | Wed/ | | | | | | | | |
| Thr/ | | | | | | Thr/ | | | | | | | | |
| Fri/ | | | | | | Fri/ | | | | | | | | |
| Sat/ | | | | | | Sat/ | | | | | | | | |
| Sun/ | | | | | | Sun/ | | | | | | | | |
| Mon/ | | | | | | Mon/ | | | | | | | | |
| Tue/ | | | | | | Tue/ | | | | | | | | |
| Wed/ | | | | | | Wed/ | | | | | | | | |
| Thr/ | | | | | | Thr/ | | | | | | | | |
| Fri/ | | | | | | Fri/ | | | | | | | | |
| Sat/ | | | | | | Sat/ | | | | | | | | |
| Sun/ | | | | | | Sun/ | | | | | | | | |
| Mon/ | | | | | | Mon/ | | | | | | | | |
| Tue/ | | | | | | Tue/ | | | | | | | | |

Fertility Calandar Key:

▦ Cells (Not Fertile)   Love Making ♡   Ferning (Fertile) 🐦
Canals (Maybe Fertile) ▨   ☽ Menstruation (Not Fertile)
Cervical Mucous, Fertile: CR=Creamy, EL=Elastic, SL= Slippery, PT=Pasty
Cervical Mucus, Not Fertile; D=Dry, CR=Crumbly, NO=None

Figure 9b

POSITIVE FERTILITY TESTING AND REPRODUCTIVE HEALTH SYSTEM

INTRODUCTION

This Invention relates to a fertility analysis and reproductive health system. In particular the Invention is a portable, hand-held, integrated unit which can be manufactured out of plastic. The unit can be disposable for hygienic purposes, or cleaned or sterilized for repeated use as desired.

Aspects of the present Invention include the unique, immediate testing methodology employing any and all female fluids or secretions called Positive Fertility Testing, "PFT," to perform fertility and reproductive analysis, unlike prior art devices. All female fluids and secretions convey key, universal, hormonal, enzyme, or other chemical carriers which under the Invention's analysis the user can determine whether or not a woman is positively ovulating and fertile. The Invention will allow the user to see crystalline "fern" patterns for tracking positive ovulation, making the Invention nearly 100% effective for determining the time of ovulation. This makes the Invention far superior to other prior art devices.

Another aspect of the present Invention is that it greatly simplifies the testing process and results in numerous economies. For instance, unlike many alternative systems, the Invention does not require a prolonged period of time to perform the analysis, nor are comparative tests required to get extremely accurate readings. However, the Invention can perform multiple confirming tests simultaneously by using the same or different female fluid or secretions. In this way the Invention can immediately provide information on the positive or negative status of a women's fertility and the condition of her reproductive health.

The Invention may be used without extensive training. Furthermore, the device and its associated processes are based upon a visual reference system designed to be language independent so that it can be used anywhere in the world and in areas where the user may in fact be illiterate.

Because the Invention can tell the user when positive ovulation has occurred it can help a woman prevent or postpone pregnancy, or assist a woman in becoming pregnant naturally, as desired. The Invention is accurate during any reproductive situation, including breastfeeding, premenopause, after the discontinuation of medication including, contraceptive pills, and during times of illness or stress. For women having difficulty becoming pregnant the Invention can help identify many specific infertility problems relating to reproductive health.

The Invention can support or reduce the use of other contraceptives and support or reduce the use of other ovulation test methods. However, the Invention may also be used as a stand-alone birth control device or reproductive health tool. Other prior art devices are physically invasive, time consuming, cumbersome and onerous. Traditional prior art devices interrupt or halt intimacy. For women using the Invention, loving and sexual feelings can flow into spontaneous lovemaking. The Invention not only avoids the interrupting of lovemaking, but it also eliminates the mess and often harmful side effects of contraceptive devices and chemicals. The Invention's visual display gives information directly to the woman, thus providing self-confidence, independence and security knowing just when she can or can not become pregnant.

The Invention also satisfies curiosity about the natural body processes of a woman and helps the user identify cyclic emotional swings, and treat premenstrual discomfort. In assisting in reproductive health, the Invention helps the user immediately become aware of abnormalities which may indicate infections, cysts, or other changes in a woman's gynecological health.

The Invention also has the ability to provide information as to the fertility status and reproductive health status of the male as well. Male fluids and secretions, including but not limited to, saliva, sperm and semen, may be analyzed. Issues of non-viable sperm, low sperm count, excessive testicular heat effect, impotence inducing factors, etc. can be effectively observed. It is possible to use the information from Positive Male Fertility analysis to help influence the sex of a child for couples looking to achieve pregnancy.

Moreover, integral to the Invention and its purpose are elements designed to optimize manufacturing processes and minimize assembly of optics and other components.

These unique manufacturing elements reduce costs and remove potential barriers from users who are financially unable to afford or gain access to more expensive prior art tests or equipment. Because of its high accuracy, ease of use, low cost of manufacturing, and the fact that it honors religious or personal convictions prohibiting artificial contraceptives or the use of blood or urine, it is expected that the Invention will be endorsed by religious authorities and world governments and will be distributed to support population awareness and reproductive health for both men and women.

BACKGROUND OF THE INVENTION

Preventing pregnancy in the past has centered upon either preventing the ovum from release or uterine attachment, or blocking the sperm from reaching the ovum. Collectively called Contraceptives, the types of contraceptives includes: contraceptive pills, implants, or intra-uterine devices. The latter includes: female and male condoms, diaphragms, sponges, different kinds of spermacides, chemical foams, sprays, and additives, the withdrawal of the penis prior to ejaculation, celibacy and abstinence. For those in an active sexual relationship the prospects of continual withdrawal, abstinence or celibacy are undesirable. Other problems and complaints with the prior art include the undesirable health side-effects of chemicals or implants, the mess, clean-up and the loss of spontaneity in lovemaking. Because these prior art methodologies are also not necessarily accurate or reliable and provide no feedback to the user as to whether or not they are working, there may also be an underlying fear or psychological concern involved in using them.

In addition to other problems and limitations, the prior art has not been able to accurately determine the time of ovulation. Because of this major limiting factor, products based upon these prior art technologies are unable to be effective contraceptives. For this reason, achieving pregnancy in the past has revolved around the central thesis of trying to determine when ovulation has occurred, Positive Fertility, is the optimum time for conception.

The combined capacity to achieve or prevent a pregnancy, naturally, in one technology, in addition to the ability to accurately determine Positive Fertility and provide a tool for overall reproductive health has not been possible with the prior art for a number of reasons that will become evident.

In a normally ovulating female certain chemical and physiological changes occur for a period which usually extends over a 28 day cycle. Many methodologies in the prior art have been used to compare and contrast these changes, either together or separately, in order to determine the day of a woman's ovulation. By determining the day of ovulation it can be established when a woman is fertile and can therefore become pregnant.

Prior to the Invention, which introduces Positive Fertility Testing, there have been only two primary approaches in determining fertility: *Predictive and Chemical Assay.* The first relies upon measurements and observations over a prolonged period of time to establish a rhythm and pattern upon which predictions can be made or calculated concerning when a woman may next experience ovulation, fertility, infertility, or menstruation. The second approach uses chemical analysis of specific bodily fluids to determine what state a woman is in during her regular monthly cycle.

Predictive Methodologies:

The Predictive approach suffers from the problem of the reliable, diligent and disciplined collection of data on the part of the woman and/or health practitioner over a prolonged period of time. The main categories of the Predictive method include:

(1) The Calendar Rhythm Method, which includes: the observation of menstruation over a prolonged period, changes in the uterine cervix, ovulation pain, breast symptoms, other bodily indications and the observation of changes in behavior over a prolonged period.

(2) The Basal Body Temperature Method, which includes the measurement and comparison of basal body temperature over a prolonged period.

(3) The Cervico-Vaginal Mucous Method, which includes the observation of the changes in cervical fluids over a prolonged period including subjective changes in the consistency, color, clarity, and opaqueness of cervico-vaginal fluid or objective changes in the volume of vaginal transudate.

For Predictive Methods to work with any degree of reliability, months and even years of data must be compiled. Of course, any predictions made based on this system can only be applied to the one woman whose data was collected.

Since the body is a complex system, circumstances of diet, environment, stress, age, and weight, among other factors, all effect the regular monthly cycle of a woman. Predictive Methods can not adequately forecast instances of multiple ovum release, or cycles where no ovum are released. Therefore Predictive Methods are notoriously considered the most untrustworthy.

(1) The Calendar Rhythm Method

Ovulation can and does occur any number of days after menstruation begins. Despite this fact, women using the calendar rhythm method count the number of days in previous cycles. Then they merely guess which days might be fertile in the future. Since cycle lengths normally vary, the rhythm method is usually undependable, creating pregnancy when it is desired to be avoided, or being unreliable in indicating positive ovulation so that conception can occur. Despite these inherent problems, the rhythm method has been universally accepted because of religious or personal convictions prohibiting artificial contraceptive methods.

(2) Basal Body Temperature Method

A woman's temperature in the morning, right after she awakens, is low between the time period of menstruation and ovulation. Around the time of ovulation, the temperature rises and remains high for about two weeks until the next menstrual period. The hormone estrogen helps cause the low temperatures before ovulation. Higher temperatures reflect the higher levels of progesterone hormone secreted after ovulation.

Digital thermometers are now in common use in hospitals and clinics and are now available for women to use for tracking their own Basal Body Temperature. The digital readout facilitates easy and reliable reading and a microprocessor calculates the rate of change of temperature and gives an audible sound when the temperature reaches equilibrium. A temperature probe is used to measure the Basal Body Temperature and the reading is displayed on a small liquid crystal display screen. The daily temperature readings may be stored in the computer's memory. This may help the woman to graph or track her changing temperature readings over time to help indicate when the post-ovulatory phase has begun.

There is a tremendous burden on the woman to collect her temperature at the same time, or many times, every day which may not be possible or practical. There is also the requirement to keep accurate records of these temperature measurements; for it is from these records that the woman is attempting to estimate her fertile or infertile phases. This is a significant problem and weakness in using temperature as a fertility indicator.

Moreover, after studying 20,672 menstrual cycles with Basal Body Temperature charts, Dr. Rudolph Vollman, *The Menstrual Cycle*, W. B. Saunders Co., Philadelphia, 1977, concluded that every woman's graph is unique to her. The day-to-day succession of the Basal Body Temperatures shows all possible variations within the same woman and between different women. It is difficult to define a practical number of patterns without producing abstract and potentially distorted plots. Further, the recording of Basal Body Temperature measurement can provide no particular point on the graph which indicates the day of ovulation.

(3) Cervico-Vaginal Mucous Method

It has been well established that the volume and consistency of cervico-vaginal fluid may be a key fertility indicator. There is as much as a ten-fold increase in the amount of cervico-vaginal mucous during the fertile phase with the level beginning to rise soon after menstruation, reaching a peak volume at high fertility and dropping abruptly to almost nonexistent levels after ovulation. However, while it is possible to measure these varying volumes of mucous and vaginal transudate by using a vaginal aspirator, this type of observation or testing remains highly inconvenient for the woman to perform and extremely subjective in its interpretation. This method requires the consistent tracking of the fluids over a long period of time and even then the woman is still making what amounts to an educated guess as to when ovulation may occur.

To summarize, all Predictive Methods track only specific symptomology to assist in a subjective interpretation as to the onset of the woman's fertile phase. All Predictive Methods are unable to indicate positive fertility or positive ovulation making this type of testing inconsistent and unreliable.

Chemical Assay Approaches

The Chemical Assay approach, while considerably more accurate in comparison with Predictive Methods, have their own unique problems. First of all, these methods usually require specialized knowledge, complex equipment and trained specialists to perform the required tests. These tests usually take time to perform, are frequently very expensive, and often require testing to be done in person in a medical facility where complex equipment is available. Like the Predictive approach, many Chemical Assays also require testing over a period of time to establish a pattern in order to make comparisons. Without a base of tests for comparison it is often not possible to draw correct conclusions regarding the status of a woman's cycle.

For the most part, Chemical Assay methodologies have focused on the analysis of blood or urine, or the chemicals and compounds found in blood or urine samples.

The main categories of the Chemical Assay Methods include:

(1) Hormone Assays Methods, which include: hormone assays to determine sex steroid hormone levels in blood or urine, and microfilter paper radioimmunoassays for progesterone, prolactin and other hormones.

(2) Ultrasonic Methods, which include: ultrasonic techniques used to observe follicular development.

(3) Breast Milk Assay Methods, which include: the measurement of changes in the ionic content and glucose concentrations in breast milk.

(4) Electrical Resistance Methods, which include: the measurement of the changes in vaginal electrical resistance.

(1) Hormone Assay Methods

Hormone assays to determine sex steroid levels in blood are currently the standard methodologies and techniques used in determining the fertile and infertile phases of a woman's cycle. They have the disadvantage of being tedious and costly for the woman and require a well equipped laboratory and specialized staff to perform tedious analysis efforts. The results of the hormone assays are not normally immediately available which makes them unsuitable for women who want to know their positive fertile days for conception or for natural birth control. In some instances women are hospitalized for continuous testing to try to determine an ovulation pattern and to enable medically assisted conception to occur. This is inconvenient, costly and labor intensive.

Even microfilter paper radioimmunoassays for progesterone, prolactin and other hormones have the same problems as those associated with Hormone Assays. Even though the woman can collect the blood spot or urine sample at home, the assays must be done in the laboratory and interpreted by qualified specialists. Thus radioimmunoassay results are not readily available and are associatively expensive and time and labor consuming.

Recently the use of monoclonal antibodies has led to home-based self testing kits designed to measure Luteinizing Hormone, "LH", changes in urine. OvuStick™ URINE hLH Test by Monoclonal Antibodies Inc. of the United States, detects urinary hLH by a blue color change on an originally white dipstick. Over the past decade similar home based LH kits have been produced under different brand names. Conceive™, distributed by QUIDEL Corporation of San Diego, Calif., U.S. Pat. Nos. 4,943,522 and 4,703,017, is another example of a color changing dipstick or paddle. Answer™, distributed by Carter Wallace, Inc. of New York, N.Y. relies on the observable changes of color in a test tube solution of urine combined with dried chemicals. These LH kits can not determine ovulation but rather can only predict the onset of ovulation by the increased chemical symptomology associated with ovulation. LH kits are therefore totally unable to give positive ovulation results.

All LH kits have a further limited use because they are only suitable for women wishing to achieve a pregnancy. For women wishing to avoid a pregnancy, the color change detected by LH methodologies occurs too late in the fertile phase to accommodate for sperm survival or planned abstinence. Test kits for estradiol and pregnanediol in urine have proved much more difficult to produce than those for LH. These tests also suffer from the same inherent disadvantages and limitations of LH kits.

(2) Ultrasonic Methods

The problems associated with ultrasonic techniques are that of being costly, requiring specialized expertise and demanding in that the woman be available for a daily visit to a hospital's ultrasonic department. Recent reports also suggest that ultrasonic waves may have many of the same disruptive and cumulative effects on the body as x-rays. These may make Ultrasonic Methods contraindicative for health reasons, especially for those women wishing to achieve pregnancy. Even so, it may be considered statistically impossible that an ovum would be released from its follicle consistently during ultrasonic examinations, or that the ultrasonic technician could determine from the ultrasonic test that such an release had occurred. These problems make ultrasonic techniques unsuitable for the detection of the positive fertile period.

(3) Breast Milk Assay Methods

While it is has been demonstrated that there are changes in the ionic content and glucose concentrations in breast milk occurring between fertile and infertile phases, no simple tests have been developed. Obtaining breast milk or colostrum from women who are not normally lactating as a result of recent child birth or from women in the later trimester of impregnation is also difficult. In the case of an already impregnated woman the need for fertility tracking is of no value. In the case of a woman who has recently given birth, the collection of breast milk assumes that the woman is breast-feeding when breast milk samples are readily available. Otherwise the collection of milk or colostrum would be of the same difficulty as a woman who had not given birth. For this reason tests that may be developed using this approach will have limited application.

(4) Electrical Resistance Methods

U.S. Pat. Nos. 4,557,273 and 4,246,907 teach the use of the reporting of bioelectrical potentials of ovulating women subjects in the area of their finger tips during their menstrual cycle to determine a midcycle peak potential. Another battery-powered device consists of a metal tampon-sized vaginal sensor which is connected to a handheld digital readout indicating the measured electrical resistance in the vagina.

Summary of Prior Art Characteristics

In summary, many of these prior art Chemical Assay Methods require that fertility testing must be conducted within a specific period of time, such as after acquiring the body fluid samples, because of the perishable nature of the samples or the fact that the accuracy of the test decays with the age of the sample. Further, many prior art tests have the requirement that they must be performed by a qualified technician, doctor or health practitioner. Usually these tests must be conducted at a specific location, because of the need to use heavy, expensive or specialized equipment to take samples, perform the test, acquire data, and conduct the analysis. For this reason the tests usually must be conducted in a facility like a clinic or hospital thus making them impractical or prohibitively expensive to most women. Moreover, the equipment or qualified personnel may not be available near a woman's residence, thereby making most Chemical Assay testing impossible to perform for these women.

Predictive Methods are untrustworthy since the body is a complex system where the governing factors of diet, environment, stress, age, and weight, among others, all affect regular monthly cycle of a woman. Despite these inherent problems, Predictive Methods like the Rhythm Method have been universally accepted because of religious or personal convictions prohibiting the use of blood for testing or any type of artificial contraception.

Further, and most significantly, neither the Predictive Methods nor the Chemical Assay Methodologies can determine positive ovulation. Most chemical assay tests, like the LH tests, show chemical color changes indicating fertility too late to prevent conception and avoid pregnancy if it is not desired.

As previously stated, prior art Contraceptive methods cause undesirable health side-effects because of the chemicals or implants used, are messy, often burdensome creating the loss of spontaneity and providing no feedback to the user as to their effectiveness.

In conclusion, all of these factors show the restrictive nature of all prior art methodologies which are illustrative of the significant differences between them and the Invention. In view of the disadvantages with traditional fertility analysis methods, whether they are Contraceptives, Predictive Methods or Chemical Assays, it is desirable to produce an improved positive fertility test system that overcomes these disadvantages.

SUMMARY OF THE INVENTION

The present Invention has numerous aspects. These aspects include:

(1) A unique, immediate testing methodology employing any and all female fluids or secretions called Positive Fertility Testing (PFT), (2) The creation of a plastic, completely integrated, portable, self-contained and self-focusing Examination System which relies on a visual reference making it language independent, (3) A Test Area Section with replaceable slides where different, specific wavelengths of light are employed, (4) The embodiment of compound test areas so that multiple Positive Fertility Tests may be conducted simultaneously, (5) Implementing the ability to immediately perform two or more Positive Fertility Tests simultaneously using different female fluids or secretions, (6) Providing a novel battery powered microprocessor system to automatically perform Positive Fertility Testing, (7) The embodiment of the most accurate indicator of positive ovulation whereby the woman may pinpoint times of greatest fertility, thereby knowing the optimum time period for achieving pregnancy. Alternatively, the use of the Invention as a birth control device; or to identify hormonal imbalances, irregular cycles or infertility. the invention may also be employed to introduce young women to their fertility cycle, enhance creativity, sexuality and health.

(8) The embodiment of a unique, immediate testing methodology employing male fluids and secretions, including saliva, semen and sperm for determining the reproductive health and fertility status of a male.

One aspect of the present Invention is the unique, immediate testing methodology employing any and all female fluids or secretions called *Positive Fertility Testing*. All female fluids and secretions convey key, universal, hormonal, enzyme, or other chemical carriers. When any female fluid or secretion is collected, dried and examined it can be determined immediately by the tell-tale, visual reference pattern of these key, universal carriers whether or not a woman is positively ovulating and fertile. This greatly simplifies the testing process and results in numerous economies.

A second aspect of the present Invention is the creation of a plastic, completely portable, self-contained and self-focusing, PFT Examination System which relies on a visual reference process, making the Invention language independent and ensuring the device can be used by people who may in fact be illiterate. The PFT Examination System consists of two interlocking sections, the Viewing Section and the Testing Area Section, which rotate along a central connecting joint. By having the PFT Examination System be manufactured as an integrated piece of injectable plastic, or formed using vacuum-form type processes, it will be made initially sterile during the manufacturing process. If required for hygienic purposes, the entire PFT Examination System once used for Positive Fertility Testing may be disposable. In the alternative, only the Testing Area Section or their subcomponents may be disposable after use. The selection of plastic and its finish is important so that the PFT Examination System may be easily cleaned or resterilized. An important element is to use plastic materials to construct the Examination System which are non-toxic and free from additive chemicals and are acceptable for human use by the United States Food and Drug Administration. The central connecting joint ensures that the Viewing Section and the Testing Area Section will maintain a distance from each other, creating proper self-focusing between the two sections. However, should any fine focusing adjustment be required, for instance in the case of those who might wear corrective lenses or glasses, then the central connecting joint allows for this fine focusing to be easily accomplished. The combination of these factors make the PFT Examination System an integrated testing system with numerous benefits and economies.

A third aspect of the present Invention is a Test Area Section with replaceable Examination Slides where different, specific wavelengths of light are employed. These specific wavelengths of light may be directed into the PFT Examination System by using Examination Slides built into the Test Area Section which are formed of plastic or plastic-like materials which have specific transparency, translucence, opaqueness, light absorbing, light reflecting or other desirous light wave properties. The combination of these factors make the Test Area Section safe and easy to use, giving rise to numerous other benefits and economies.

A fourth aspect of the present Invention is the embodiment of compound test areas so that multiple, confirming Positive Fertility Tests may be conducted simultaneously. To the extent that multiple confirming tests were required using prior art testing techniques they demand the use of totally separate, non-integrated testing devices. Testing with the prior art can not be conducted in an integrated unit because an integrated unit would be even more cumbersome and could result in contamination of the samples with chemicals from one test area to another. Since the present invention employs no chemicals, but rather light wave properties to perform Positive Fertility Testing, multiple tests may be conducted without concern of chemical contamination. Further, these multiple tests may be conducted on Examination Slides which use or embody different light wave properties to allow the user better visual reading of the results of the Positive Fertility Testing. By creating multiple test areas the incidence of any possible misreading is reduced to negligible amounts and a psychological comfort in the Positive Fertility Testing is increased. The embodiment of these compound test areas gives rise to numerous other benefits and economies.

A fifth aspect of the present Invention is implementing the ability to immediately perform two or more Positive Fertility Tests simultaneously using different female fluids or secretions. This embodiment creates quantifiable and qualitative increases in accuracy and emphasizes the ability of the Invention to provide nearly 100% precision in determining time of ovulation thus providing additional psychological comfort to the user. This aspect of the Invention enhances the woman's ability to prevent or postpone pregnancy naturally. Because the Invention allows women the choice of which fluids or secretions or combinations of fluids or secretions to use for Positive Fertility Testing, the Invention honors religious or personal convictions regarding the use of bodily fluids. Therefore any prohibitions, misgivings, or health concerns against the use of blood or urine will not be violated since the accuracy of the Positive Fertility Testing and the ability to perform multiple tests with different fluids will not be compromised by using, for example, saliva, cervical mucous, tears, breast milk, nasal mucous, or vaginal transudate, etc.

A sixth aspect of the present Invention is providing a novel battery powered microprocessor system which uses Liquid Crystal Display and Light Emitting Diodes to automatically perform the Positive Fertility Testing.

A seventh aspect of the present Invention is the embodiment of the most accurate indicator of positive ovulation whereby the woman may pinpoint times of greatest fertility, thereby knowing the optimum time period for achieving pregnancy or in the alternative the use of the Invention as a birth control device. Because of its extreme accuracy the embodiment can reduce or eliminate contraceptive usage; it can identify hormonal imbalances, irregular cycles or infertility; introduce young women to their fertility cycle, enhance creativity, sexuality and health.

A eighth aspect of the present Invention is the embodiment of an accurate and immediate testing methodology to provide information as to the fertility status and reproductive health status of a male. Male fluids and secretions, including but not limited to sperm and semen, may be analyzed. Issues of non-viable sperm, low sperm count, excessive testicular heat effect, impotence inducing factors, etc. can be effectively observed.

Finally, other aspects of the present Invention will become apparent from a reading of the "Detailed Description of Preferred Embodiments" and a review of the accompanying drawings.

BRIEF DESCRIPTION OF THE DRAWINGS

FIG. 3 shows a front cutaway view of the of the present Invention displaying the Testing Section;

FIG. 4 shows a rear view of the present Invention displaying the Testing Section;

FIG. 5A shows a view of the present Invention illustrating the integration of the Viewing Lens Section with the Testing Area Section with the ability of the two sections to rotate about a central joining axis.

FIG. 5B shows a side sectional view of the present Invention showing both the Viewing Lens Section and the Testing Section;

FIG. 5C shows a view of another preferred embodiment of the present Invention, a Male Personal Fertility Examination System, illustrating the integration of the Viewing Lens Section with the Testing Area Section with the ability of the two sections to rotate about a central joining axis.

FIG. 6A shows an illustration of a sample testing slide result from the present Invention showing positive ovulation fertility signs;

FIG. 6B shows another illustration of a sample testing slide result from the present Invention showing positive ovulation fertility signs;

FIG. 6C shows an illustration of a sample testing slide result from the present Invention showing negative fertility signs indicative of pre-ovulation;

FIG. 6D shows another illustration of a sample testing slide result from the present Invention showing positive ovulation fertility signs;

FIG. 6E shows an illustration of a sample testing slide result from the present Invention showing negative fertility signs indicative of post-ovulation;

FIG. 6F shows an illustration of a sample testing slide result from the present Invention showing canalization, indicative of pre-ovulation;

FIG. 6G shows an illustration of a sample testing slide result from the present Invention showing negative fertility signs indicative of post-ovulation;

FIG. 6H shows an illustration of a sample testing slide result from the present Invention showing Male Universal Fertility Indices.

FIG. 6I shows another illustration of a sample testing slide result from the present Invention showing Male Universal Fertility Indices.

FIG. 6J shows an illustration of a sample testing slide result from the present Invention showing spermatozoa in seminal fluid.

FIG. 9B is one example of a calendar chart where a woman may record her Positive Fertility Testing results.

DETAILED DESCRIPTION OF PREFERRED EMBODIMENTS

Figure 1:
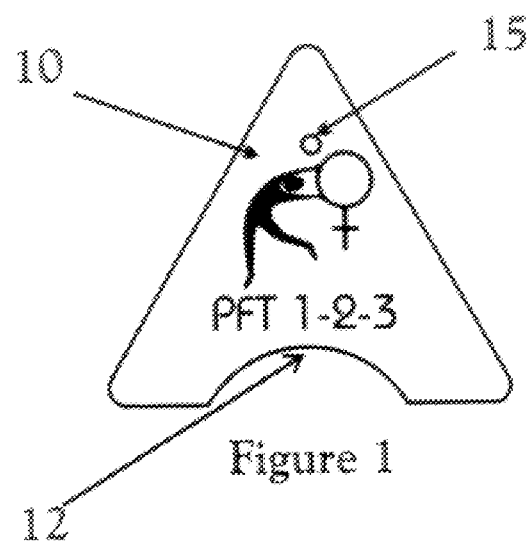
FIG. 1 shows a front view of the preferred embodiment of the present invention displaying the Viewing Lens Section.

The present Invention has numerous aspects which contribute to the versatility and economy of design and performance, particularly in creating an integrated fertility examination system embodying a new, reliable category of birth control, fertility awareness and reproductive health called Positive Fertility Testing.

(1) Positive Fertility Testing

All female fluids and secretions convey key hormones, enzymes, salts, and other chemical carriers called Key Fertility Interactors. "KFI." Some KFI include, but are not limited to, estrogen, progesterone, LH, Follicle Stimulating Hormone, "FSH," pregnanediol, prolactin, salivary estradiol, progesterone, glucose, electrolytes (sodium and potassium), salts and enzymes. KFI are present in all female fluids and secretions including saliva, cervico-vaginal fluid "CVF," tears, nasal discharge, breastmilk, blood, urine, spinal fluid, and cervical mucous. The levels of individual KFI vary continually over the cycle of a woman. They are also unique to each woman and as can be anticipated, the levels of KFI are distinct at any given moment in time. Prior art methods have focused on determinative testing to achieve interpretations of what the discreet levels of individual KFI may signify. Accumulating test samples of fluids which contain sufficient quantities of KFI for assay has been problematic as discussed. Keeping testing samples from perishing or free from contamination while under analysis has been equally challenging.

The present Invention offers a completely different approach. Rather than looking at individual KFI or combinations of KFI, as the prior art teaches, the Invention formulates a new methodology, process and approach by examining the overall interactions which these KFI create among themselves. KFI form unique interactions with one another throughout a cycle of a woman. However, these interactions are universal for all women. Therefore KFI form electrochemical interdependencies which convey Universal Fertility Indices, "UFI " While KFI testing presents limitations and problems, testing for UFI does not. Unlike KFI, UFI is testable regardless of concentration levels in all female fluids and secretions. UFI can be consistently tested for and uniformly interpreted with great accuracy for all women. PFT testing for UFI at once results in a remarkable simplification of the fertility testing process and causes numerous benefits and economies.

UFI may not be observed with the unaided eye. UFI may not be observed unless the sample has been collected and prepared in the manner specified. When this is successfully accomplished from any female fluid or secretion collected, it can then be determined immediately by the tell-tale, visual reference pattern of these UFIs whether or not a woman is positively ovulating and fertile. In addition to her fertility status, the size and shapes of the patterns of UFI observed, i.e. amorphous, canalized, randomized cells, noise, crystals, fern, snow-flake, etc. provide tremendous amounts of information as to the immediate reproductive health and gynecological status of the woman.

There are three steps in Positive Fertility Testing. First is the collection and preparation of the PFT sample(s). Second is the viewing of sample(s) under magnification and using the proper wavelength of light. And Third is the interpretation of the results of the PFT which includes, but is not limited to, the recording and the comparison of prior PFT results.

Figure 2:
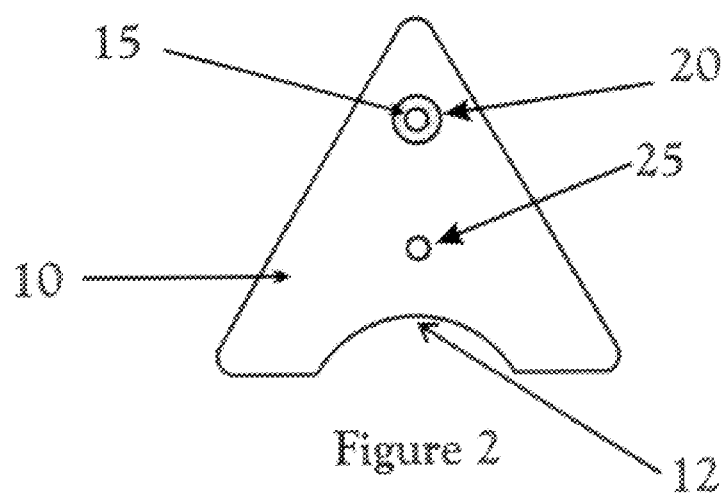
FIG. 2 shows a rear view of the present Invention displaying the Viewing Lens Section.

(A) The Collection of the Sample(s). FIG. 5A shows one example of a preferred embodiment of an integrated PFT Examination System. The PFT Examination System incorporates a small high powered numberal 15 microscope which allows the user to see the crystalline patterns of the UFI. The PFT Examination System is in the shape of a triangle with two disks that rotate from a center axis. FIG. 1 and 2 show that Microscope Bead Lens 15 serves as the objective lens for the microscope and is housed in the upper disk Viewing Section 10. FIGS. 3 and 4 show that Test Area Section 30 serves as an integrated microscope stage, PFT sample collecting and testing area and testing slide receptacle. In one preferred embodiment, Testing Area Section 30 Consists of three Examination Testing Slides, 50, 55 and 60 which are colored clear, yellow and red respectively.

Any female fluid or secretion may be collected and used because they all contain sufficient UFI to perform PFT analysis upon. In one preferred embodiment, however, the Invention system uses a normally ovulating woman's saliva to perform the PFT analysis upon because it is usually the easiest for her to obtain. The use begins with a PFT Examination System which is sterile or clean. When saliva is used, it is recommended that the woman analyzing her UFI not eat or drink fluids 30 minutes prior to PFT testing as this may dilute saliva and alter results. Often it is easier for a woman to PFT her saliva at the beginning of the day before she has had anything to eat or drink.

The user rotates the top triangle of, Viewing Section 10, of the PFT Examination System, so the Clear Slide 50 on Testing Area Section 30 is easily accessible and facing upward toward them. The user then licks the top of Clear Slide 50 so that it makes an even, thin film of saliva. The user then rotates the top triangle of viewing section 10 and licks both the red and yellow slides 53 and 68, respective. Next the slides are allowed to dry completely. It is recommended that a natural drying process be used, however the drying process may be accelerated, for instance, by placing the sample near a light bulb or in a place where the sun shines such as a window sill.

Cervical fluid can also be used for testing instead of saliva or to verify the PFT findings if the result of the saliva test is in any way uncertain. If the woman has any inflammation in her mouth or throat or if she drank liquids or ate food just before doing a test, it is recommended that cervical mucous be substituted for saliva. In order to access the vagina comfortably, elevate the left foot slightly by placing it on a foot stool or other raised object. With her right hand, the woman gently inserts a clean finger completely into the vaginal opening. The mucous will stick to the inserted finger as it is withdrawn. A sterile swab, speculum or other type of probe may be used to gather a cervical fluid specimen specimen. The mucous is then deposited onto Test Slide 55 and allowed to dry. It is also possible to conduct a combined testing using both saliva and cervical mucous by placing saliva samples on Test Slide 50 and cervical mucous on Test Slide 55.

The UFI crystal formations of the cervical mucous tend to be more clearly identifiable. However, cervical mucous readings may not be accurate if diluted or mixed with menstrual blood, seminal fluid, or during a time of vaginal infection. Swimming, bathing or douching is not recommended prior to collecting a sample. Also, a sample which is too thick may be difficult to read. In cases of suspected vaginal infection, itching, inflammation, or changes in the characteristics of the fluid, saliva or another female fluid or secretion such as tears, or urine should be used.

(B) The Viewing of the Sample(s). In the preferred embodiment, the PFT Examination System is a completely self contained system so that once the saliva sample has dried in the test area, the visual result of the PFT analysis may be obtained instantly. The accuracy of the PFT analysis on UFI does not degrade over a reasonable time if the woman is unable to view the test immediately after their saliva sample has dried or if the woman wishes to have a doctor or other health practitioner view the slide for a second opinion. If desired, the entire PFT Examination system may be mailed or sent to a third party. In the alternative FIG. 5B shows how Testing Area Section 30 may be detached from central connecting joint 25 so that only it Testing Area Section 30 need be supplied to a third party. A new, clean Testing Area Section 30 may be easily attached by inserting Central Connecting Post 65 into central connecting joint.

To view the sample once it has dried, the top triangle of the PFT Examination System, Viewing Section 10 is rotated, so that Microscope Bead Lens 15 is directly above and centered over Test Slide 50. The PFT Examination System is easily grasped between the thumb and forefingers in the center of the device. The user holds the PFT Examination System about a ½ inch from the eye and looks through Microscope Bead Lens 15. If necessary, the PFT sample can be brought into focus by gently squeezing the triangles of Viewing Section 10 and Testing Area Section 30 together. Finger pressure may be varied until the objects on Test Slide 50 appear in clear focus. Some UFI are not visible unless viewed under certain lighting conditions or using specific wavelengths of light. Using fluorescent, diffused light or direct sunlight may make it harder to see the results. In this case it is recommended that the PFT sample is collected and deposited on yellow Test Slide 55 or red Test Slide 60 if these types of light sources are employed. More specific information relating to viewing under the proper and appropriate wavelengths of light is contained in the hereinafter section entitled, (3) A Test Area Section With Replaceable Slides Where Different, Specific Wave Lengths of Light Are Employed.

While not required, it is suggested that a woman choose a specific time every day when PFT testing can be consistently accomplished. In this way PFT analysis can become a regular function of the morning, or daily routine. Some women may choose to test two or more times a day to confirm results or note any change—especially during the fertile phase of the cycle.

(C) The Interpretation, Recording and Comparison of PFT Results. Because of KFI interactions in female fluids or secretions, some of which may occur upon drying of the sample, or the exposure of the PFT to specific wavelengths of light, UFI are revealed which delineate distinct and visible tell-tale patterns. The patterns may be viewed, interpreted, recorded and compared. The assessment of canalization and crystallization of UFI in saliva, cervical mucus and other female fluids and secretions and their variability during the menstrual cycle has revealed a direct relationship with ovarian hormone levels and with specific physiological states, conditions and circumstances.

These UFI patterns revealed under PFT includes, but are not limited to, UFI patterns which indicate the (1) The beginning of the Fertile Phase, where the follicle is preparing to release an ovum just prior to the onset of ovulation; (2) The Full Fertile Phase, the release of ovum, actual ovulation; (3) The Nurturing phase, post ovulation, the end of which usually marks the termination of the Fertile Phase; (4) The beginning of the Infertile Phase, characterized by the breakdown of the corpus luteum in preparation for menstruation if conception has not occurred; (5) The Cleansing Phase, menstruation, which has the lowest concentration of KFI indicators; (6) The Middle Infertile Phase, post menstruation which characterizes the beginning of the Building Phase; (7) The Full Building Phase or, early preovulatory period.

The Infertile Phase begins to subside as correspondingly higher concentrations of KFI are available in preparation for the body's entering the fertile phase. Since the ovum survives only twelve to twenty-four hours after ovulation, the Fertile Phase is of an extremely short duration compared to the rest of the cycle. UFI patterns which indicate fertility are therefore important to recognize. UFI patterns observed using the PFT Examination System which indicate fertility and positive ovulation are clear and unmistakable and correspond exactly to the actual physiological conditions associated with fertility and positive ovulation.

One skilled in the art can verify that the hormone dependence of saliva and cervical mucous is clearly identified in UFI during the fertile phase, while saliva and cervical mucous seem to be hormone independent during the infertile phases. Other female fluids and secretions exhibit the same UFI morphological manifestations due to these same KFI interactions found in saliva and cervical mucous. This is because one of the components of UFI is hormone dependent while the other is hormone independent. In addition the quantity modifications, by such components of individual KFI are quite opposite during the menstrual cycle. For this reason, the observable patterns of both canalization and crystallization of UFI seen in test samples viewed using the PFT Examination System during the early preovulatory and the late postovulatory phase (prior to menstruation), show that these patterns exhibit similar morphological features in spite of the striking difference in hormonal and other KFI levels.

Closer scrutiny of the morphological features of these patterns reveals that there are additional pattern indicators that clearly correspond with the physiological conditions associated with either the preovulatory or the late postovulatory period. This verifies that there are supplementary, embedded UFI patterns or modifiers of UFI Patterns that are developed from KFI interactions other than hormonal interactions. This may explain why it has been observed that some test samples appear to continue to exhibit morphological changes for an extended period of time.

Figure 9A:
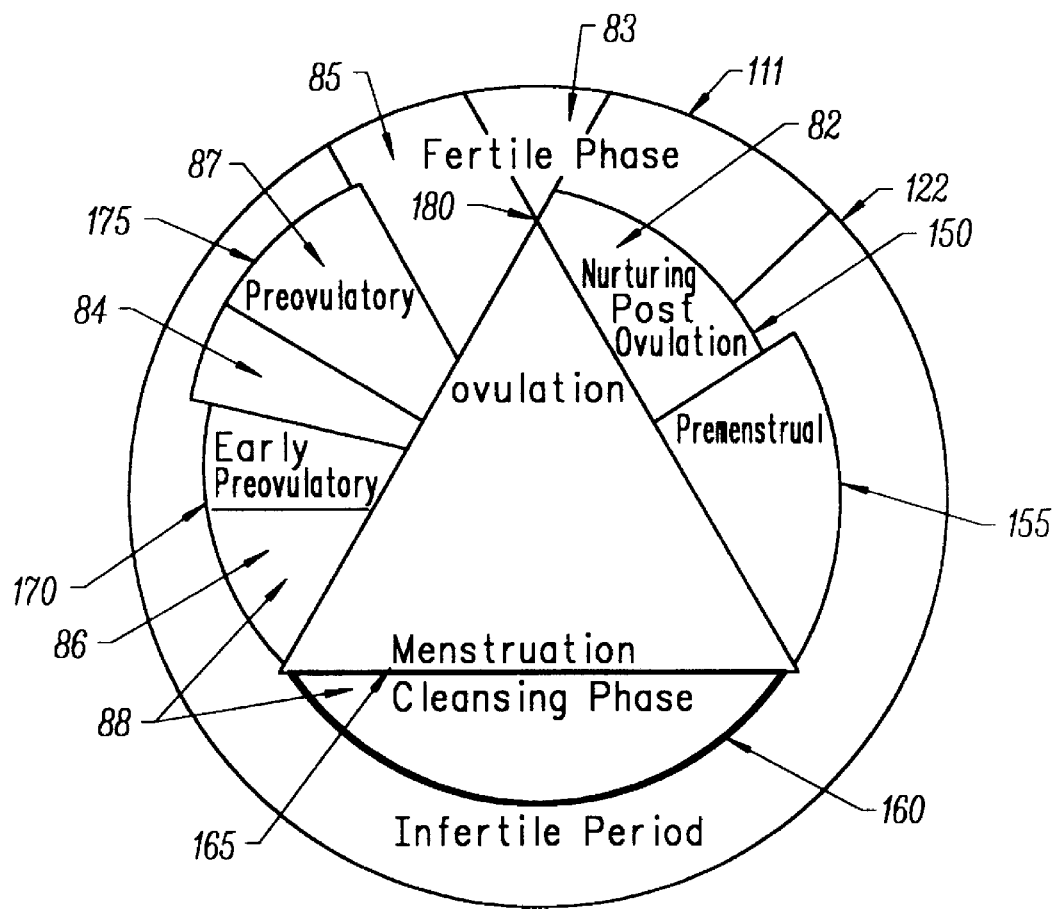
FIG. 9A is a graph showing the Universal Fertility Indices that are seen in Positive Fertility Testing during a woman's cycle.

When these special types of test samples are observed using the PFT Examination System and compared with fresh samples, the observable UFI patterns in the original sample correspond to those UFI patterns seen in the newly taken sample. PFT Patterns of UFI indicate the following:

(1) The Beginning of the Fertile Phase. FIG. 9A shows early preovulatory phase 170 which moves to preovulatory phase 175 in a women's cycle. FIG. 6C shows Randomized Amorphous Patterns 84 which are indicative of a non-fertile condition. It is so named because the observed pattern of UFI crystals take on a random cell-like shape. This classification of observable PFT Pattern of UFI is typical of the transition between the Early Preovulatory period 170 and the Preovulatory phase 175. The combination of period 170 and phase 175 is considered the Building Period.

FIG. 9A shows where in a woman's cycle Randomized Amorphous Patterns 84 most likely appear. Subsequently to Randomized Amorphous Patterns 84 a more regular channeling develops and becomes pronounced. This is due to the rising levels of Estrogen and other KFI which characterize UFI development from Randomized Amorphous Patterns 84 to UFI patterns of increased regularity. As the cycle continues, Patterns 84 mixed with the classification of observable PFT Pattern of UFI called Canalization 87 seen in FIG. 6F develop.

FIG. 9A shows where in a woman's cycle full Canalization 87 patterns begins to manifest. The early phases of Canalization are not fertile. However, because sperm may survive up to 5 days under proper conditions a woman must consider the later, more regular patterned Canalization 87 to be possible fertile times in anticipation of ovulation. This is the observable UFI Pattern that marks the transitional boundary between the Infertile Period 122 and the Fertile Period 111.

The onset of ovulation is indicated by FIG. 6D where Beginning Ferning 85 has occurred. Beginning Ferning is an immediate post Canalization materialization. It is possible that Canalization 87 and Beginning Ferning 85 may be seen in different areas on the same samples. This is the observable UFI Pattern that marks the transitional boundary between the Building Phase and the Full Fertile Period. In this case ovulation is immediately imminent or occurring.

(2) The Full Fertile Phase, the release of ovum, actual ovulation. FIG. 9A shows the Periovulatory phase 175 which moves to Nurturing, Postovulatory phase 150 in a women's cycle. FIG. 6B shows an example of the classification of observable PFT Pattern of UFI called Full Ferning, or Full Crystallization 83, indicating that Positive Ovulation 180 has occurred. FIG. 9A shows ovulation and where the associated pattern of Full Crystallization 83 is on the cycle.

(3) The Nurturing Phase, immediate post ovulation. The Nurturing, Postovulatory phase 150 typically lasts between twenty-four and forty-eight hours after ovulation. FIG. 6A shows an example of the classification of observable PFT Pattern of UFI called Broad Ferning 82. It shows the largest and most fully-developed crystallized fern patterns which is typical of the Nurturing Phase 150. The Nurturing Phase 150 is normally associated with a relative decrease in estrogen occurring in concert with a rapid rise in progesterone levels. This physiological condition observed in the UFI from PFT analysis marks the transitional boundary between the end of the Fertility Phase 111 and the beginning of the Infertile Period 122. FIG. 9A shows where this ordinarily occurs in a woman's cycle. Beyond this point the progesterone and estrogen levels generally reach a plateau around the middle of the postovulatory phase 150 just prior to the onset of menstruation.

(4) Preparation For menstruation. FIG. 9A shows where in the woman's cycle the Premenstrual Phase 155 occurs. The corpus luteum has a life span typically often to twelve days. The corpus luteum will begin to degenerate in the absence of fertilization which results in a viable conception and pregnancy. As the source of estrogen and progesterone and other KFI are eliminated or reduced the endometrium prepares to be shed. PFT Samples of UFI observed during this period show a rapid decline from dense organized forms to more sparse randomized shapes and "noise." The only exception to these kinds of UFI patterns is if a second ovum is released. In a single cycle a woman may have multiple ovum releases. PFT can conclusively show when positive ovulation occurs for one ovum or for multiple ovum, i.e. fraternal twins (ovum released and fertilized within 24 hours of each other), or ovums released over a more extended time frame. Even though multiple ovums may have been released over Nurturing Phase 150 and Premenstrual Phase 155 usually the woman will have only a single menstruation. It is also possible for a woman to have no ovum released and therefore show no observable UFI pattern in PFT analysis associated with positive ovulation in a cycle, yet have a menstruation.

(5) The Cleansing Phase, Menstruation. Menstruation 165 is shown in FIG. 9A. During Menstruation 165, the endometrium is released in the menstrual flow. At this point KFI are at their lowest levels. If PFT analysis is taken at this time the observable pattern is nearly entirely devoid pattern 88 of FIG. 69 with occasional small amorphous cells or small groups of cubic crystals.

(6) The Middle Infertile Phase, Post Menstruation. The end of Menstruation 165 marks the transitional boundary to the Building Period. The low level of estrogen and other KFI in the circulation causes the hypothalamus to initiate a new cycle of ovarian follicular development. FIG. 6G shows a sample pattern that may be expected to be collected during and after Menstruation. This is the observable UFI Pattern called the Low Cell Phase 88.

(7) The Full Building Phases Preovulatory Period. The Preovulatory Phase 175 is shown in FIG. 9A. Between the end of Menstruation 165 and the onset of Random Amorphous Patterns 84, the number of isolated crystal cellule and small vacuole groups grows from the observable UFI seen in the Low Cell Phase 88 (early preovulatory period 170) to a more organized form with larger more defined structure of stratified vacuole groups. This observable UFI pattern is called Strata and Vacuole 86 as seen in FIG. 6E. It is the onset of this UFI pattern which generally marks the transitional boundary between the Early Preovulatory Period 170 and the Preovulatory Phase 175. In FIG. 9A it can be seen where the number of cells in Low Cell Phase 88 increases after menstruation and the observable UFI pattern shifts to Strata and Vacuole 86. The Low Cell Phase 88 then moves completing into the full stages of the Building Period with increases in KFI resulting in UFI patterns similar to those of Random Amorphous Patterns 84.

Other UFI Indications Of PFT Analysis. Because UFIs create distinct patterns accurately indicating physiological conditions they are able to report not only conditions of normal gynecological health, but also those of an abnormal reproductive situation or circumstance as well. For example it is not usual that Random Amorphous Patterns 84 and Beginning Ferning 85 would be seen in different areas on the same PFT samples because this would be a contraindicative condition. Similarly small snowflake-like or ice-like crystals may indicate positive ovulation and also that a woman's estrogen level is low. All of these patterns and combinations indicate a potential hormonal or chemical imbalance which may affect fertility. The user may want to consult with a medical practitioner, health professional, or fertility and reproductive counselor. Because the UFI patterns are not limited to just fertility, but give results as to gynecological health, PFT analysis is suitable for women who have had hysterectomies, or are sterile, women who are entering or are experiencing menopause and for young girls transitioning from puberty and entering adolescence.

Anyone skilled in the art can appreciate there are innumerous patterns and combinations of UFI that are possible, including infertility, fertility and pregnancy, as well as other patterns and interpretations of PFT indicative of the condition and status of reproductive health. Those represented herein are merely illustrative and are by no means meant to limit the scope of the Invention.

(2) Integrated PFT Examination System

FIG. 5A shows one preferred embodiment of an Integrated PFT Examination System. The PFT Examination System is a plastic, completely portable, self-contained and self-focusing unit. No other test equipment, chemicals, or apparatus are required in order for the user to conduct the PFT analysis. In the preferred embodiment the Invention is hand-held, about the size of a lipstick case or compact. Because of the Invention's small size combined with its self-contained nature it allows the device to be easily carried on or about a person who can use it independent of location.

FIG. 5A shows Viewing Section 10 and Testing Area Section 30 which may be made of high density polyethylene, "HDPE," or high density polypropylene "HDPP," either available from Mobile Corporation of the United States. The HDPE or HDPP selected should be free from additives and accepted for use by the United States Food and Drug Administration for oral contact.

In one embodiment the thickness of Viewing Section 10 is 0.060 inches and Testing Area Section 30 is 0.080 inches to ensure optimum cycle time in automatic plastic injection machinery. However, other dimensions of thickness are of course possible. Other types of manufacturing processes may be employed by those skilled in the art of plastic manufacturing such as vacuum forming, catalyst activated laserography, computer or numerically controlled equipment, etc. Other types of plastic manufacturing processes may be used which will result in the suitable formation of the PFT Examination System. Materials other than plastics may also be employed, such as metals or composites; however, an important consideration is to always use materials to construct the Examination System which are non-toxic and free from additive chemicals. Attention should be given to the selection of materials and finish, i.e. rough, smooth, etc., so that the PFT Examination System may be easily cleaned or resterilized. An important design element of the preferred embodiment is low cost, high volume, automated manufacturing and assembly processes.

Viewing Section 10 and Testing Area Section 30 are made to conform to a shape which may be easily manipulated by the hand. In one preferred embodiment a triangular shape is selected with a notch 12 cut out of Viewing Section 10 and Testing Area Section 30 for easy gripping.

Viewing Section 10 holds Microscope Bead Lens 15. Microscope Bead Lens 15 is made out of high optical quality, borosilicate quartz glass balls formed by raising rods of borosilicate to the melting temperature, cutting the rods and having the molten droplets received into hot oil where the drops are then rolled, pressed and cooled into a spherical shape. Spheres formed by molding processes where two separate halves are joined together are not acceptable because the joining line across the sphere creates an ocular impairment rendering Microscope Bead Lens 15 unsuitable for use. While other processes known to those skilled in the art of optical glass formation may be used, it is important that the final sphere be of high optical clarity, free from ridges, waves, bubbles, or other defects. In one preferred embodiment Microscope Bead Lens 15 is formed from high optical quality borosilicate quartz glass in a sphere three millimeters in diameter. Borosilicate spheres from Kimbal Glass, Inc. of New Jersey have yielded excellent results for Microscope Bead Lens 15. Other sizes may be used, however changes in the fixed focusing parameters of the PFT Examination System must be correspondingly adjusted.

FIG. 2 and FIG. 5B show how Microscope Bead Lens 15 is held in place by Self-Adjusting Microscope Lens Retaining Ring 20. Self-Adjusting Microscope Lens Retaining Ring 20 forms a receiving cradle in Viewing Section 10 and includes a hole formed in Viewing Section 10 of a diameter approximately 20 percent less than that of Microscope Bead Lens 15. In one preferred embodiment this is 0.100 inches. The thickness of Self-Adjusting Microscope Lens Retaining Ring 20 should be greater than 50 percent of the diameter of Microscope Bead Lens 15 to ensure good retention, but no more than 75 percent of the diameter of Microscope Bead Lens 15 to ensure maximum light gathering and viewing capacity. The diameter of Self-Adjusting Microscope Lens Retaining Ring 20 should not be much more than that of Microscope Bead Lens 15. In one of the preferred embodiments, the inner diameter of Self-Adjusting Microscope Lens Retaining Ring 20 is 0.120 inches with a wall thickness of 0.050 inches.

When these principals are honored, Microscope Bead Lens 15 can be held firmly in place in Self-Adjusting Microscope Lens Retaining Ring 20, forming a self adjusting seal against Microscope Bead Lens 15. Because Viewing Section 10 is formed out of HDPE, or HDPE-like material, it is pliable and somewhat elastic. Light pressure applied to Microscope Bead Lens 15 as it is pressed against Self-Adjusting Microscope Lens Retaining Ring 20 will cause Self-Adjusting Microscope Lens Retaining Ring 20 to spread apart allowing Microscope Bead Lens 15 to be inserted into Self-Adjusting Microscope Lens Retaining Ring 20. Self-Adjusting Microscope Lens Retaining Ring 20 will then try to return to its original size holding Microscope Bead Lens 15 firmly in place. Microscope Bead Lens 15 may be inserted into Self-Adjusting Microscope Lens Retaining Ring 20 by hand, by automatic insertion equipment, or by insertion or formation as part of the manufacturing processes of Viewing Section 10 by those skilled in the art.

In FIG. 2 Central Connecting Joint 25 performs several functions. Central Connecting Joint 25 holds Testing Area Section 30 by corresponding Central Connecting Post 65. When pressed together Central Connecting Joint 25 and Central Connecting Post 65 form a rotating joint of a determined fixed distance between Viewing Section 10 and Testing Area Section 30. In one preferred embodiment, Central Connecting Post 65 has raised lip 70 as shown in FIG. 5B. When joined, Viewing Section 10 and Testing Area Section 30 are held together by Central Connecting Joint 25 and Central Connecting Post 65. This connection forms a self-affixing, rotating, ball-type joint which eliminates the need for any glues, mucilages, ultrasonic welding, screws, etc. to hold Viewing Section 10 and Testing Area Section 30 in place. In this manner Viewing Section 10 and Testing Area Section 30 may become an integrated unit and are free to rotate as in FIG. 5A.

FIG. 5B shows that Central Connecting Joint 25 and Central Connecting Post 65 when joined form Distance 80 between Viewing Section 10 and Testing Area Section 30. Distance 80 is selected to form an optimal viewing focal length between Microscope Bead Lens 15 and Testing Area Section 30 of Focal Length 75. In the manufacturing process, the length of Central Connecting Joint 25 and of its counterpart Central Connecting Post 65 are made to the specification of Distance 80 to accommodate Focal Length 75. In one preferred embodiment Distance 80 is 0.120 inches and Focal Length 75 is 0.060 inches. The placement and use of Microscope Bead Lens 15 in this manner creates a magnifying power of approximately 100 power.

Because Viewing Section 10 and Testing Area Section 30 are formed out of HDPE, or HDPE-like material, they are pliable and somewhat elastic. This motion is further facilitated by Lip 70 on Central Connecting Post 65 forming a ball-type action. Therefore light finger-tip pressure applied between Central Connecting Joint 25 and Microscope Bead Lens 15 will cause a squeezing together of the edges of Viewing Section 10 and Testing Area Section 30 towards one another, thereby reducing Distance 80. Alternatively, the same type of pressure applied behind Central Connecting Joint 25 will cause an increase in distance 80. The effect of these movements provide the PFT Examination System with a fine focusing capability. Even though fixed focus may be achieved with Focal Length 75 more precise focusing is possible, if needed, for those wearing corrective lens or glasses, for example.

Holding the PFT Examination System up to one eye, the user looks into Microscope Bead Lens 15 so that Microscope Bead Lens 15 is aligned to where a female fluid or secretion has been deposited and dried for observation on Testing Area Section 30 to immediately determine PFT results. Because The PFT Examination System relies on a visual reference process it is language independent. The user can be easily trained to identify key UFI patterns, like those illustrated in FIGS. 6A–6G and their associated meanings. In this way the PFT Examination System can be used successfully by people who may in fact be illiterate.

When injection plastic molding is selected as the method of manufacturing another advantage is achieved. The temperatures used to form the plastic parts are of such a high temperature to make the Examination System initially sterile during the manufacturing process. In clean conditions, with reasonable care in the assembly process, contamination will not occur. If required for hygienic purposes, or if sterilization or cleaning materials are not available, the entire Examination System once used for Positive Fertility Testing may be disposable. Because Viewing Section 10 and Testing Area Section 30 may be separated by Central Connecting Joint 25, in the alternative, only the Testing Area Section 30 or their subcomponents may be disposable after use. This embodiment enables a new Testing Area Section 30 to be inserted via Central Connecting Post 65 into Central Connecting Joint 25, thus reforming an integrated PFT Examination System.

It will be appreciated that many changes may be made to the PFT Examination System of FIGS. 1–5 without departing from the scope of the Invention. For example, multiple Microscope Bead Lens 15s could be included consisting of different diameters creating different magnifying powers. A pair of similar Microscope Bead Lens 15s could be used to create a stereoscopic effect for easier and more accurate viewing. The Focal Length 75 distance from individual Microscope Bead Lens 15's can be regulated by individual Self-Adjusting Microscope Lens Retaining Rings 20s. In another embodiment the central rotating axis could be moved off center or moved to an edge.

In another embodiment Central Connecting Joint 25 and Central Connecting Post 65 need not be present. In this embodiment, Viewing Section 10 and Testing Area Section 30 are formed of a single sheet of HDPP or HDPP like material and folded like a clam-shell along flexible edge hinge. An extended ridge on part of Self-Adjusting Microscope Lens Retaining Ring 20 ensures proper distance 80 and focal length 75. In this configuration, the PFT Examination unit may be laid completely flat, having the added benefit of a very thin profile that can be mailed easily or stored when not in use. Fine Focusing is accomplished as previously described.

In another embodiment Microscope Bead Lens 15 is formed out of a drop of clear water, preferably of a pure, filtered or distilled nature. Self-Adjusting Microscope Lens Retaining Ring 20 in this instance becomes a retaining cup to which a single drop of pure water of approximately 3 millimeters in diameter is added. An optically clear oil, like mineral oil, could also be used. The shape of Self-Adjusting Microscope Lens Retaining Ring 20 in this case is concave with a parabolic shape and of a capacity to accommodate the precise volume of the drop of water desired. The surface tension of the drop, Viewing Section 10 and the shape of Self-Adjusting Microscope Lens Retaining Ring 20 all assist in keeping the drop in an ellipsoidal form which is desirable for magnification and optical viewing. Depending on the liquid used, Distance 80 and Focal Length 75 can be properly determined and accommodated for. In this manner magnifications greater than 80 power are possible.

Further embodiments of the Invention which include subsystems other than those specifically discussed can be included in place of, or in addition to, the subsystems described. Many such variations will be apparent to one of skill in the art. The combination of these factors make the PFT Examination System an integrated testing system with numerous benefits and economies.

(3) A Test Area Section With Replaceable Slides Where Different, Specific Wave Lengths Of Light Are Employed Some UFI are not visible unless viewed under certain lighting conditions or using specific wavelengths of light. To facilitate the examination of PFT samples, FIGS. 3 and 4 show one preferred embodiment of the present Invention which allows specific wavelengths of light to be directed into the PFT Examination System by using Examination Test Slides 50, 55 and 60 built into the Test Area Section 30 which are formed of polycarbonate, available from General Electric Corporation of the United States. Roscolene which is a 6 mil plastic-like film from Rosco Corporation of Port Chester, N.Y. has also been found to be suitable. Alternatively, other plastic or plastic-like materials, gels, films or acetates which have specific transparency, translucence, opaqueness, light absorbing, light reflecting or other desirous light wave properties may be used. The combination of these factors make the Test Area Section 30 safe and easy to use, giving rise to numerous other benefits and economies.

Figure 8C:
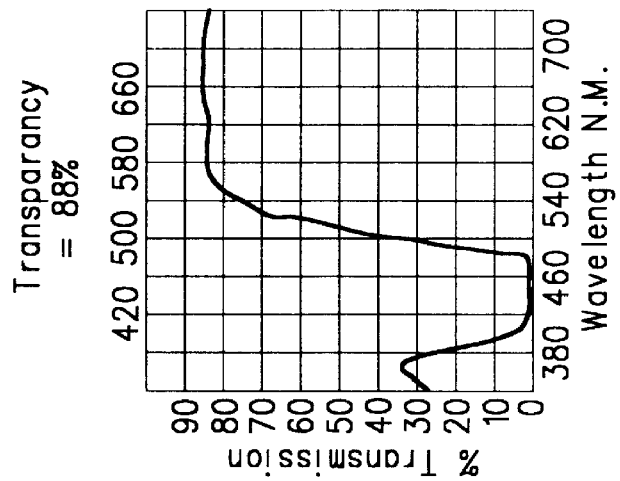
FIG. 8C is another graph of the percent of light transmission vs. the wavelength of light in nano-meters, illustrating the transparency or light wavelength characteristics of a preferred embodiment of the present Invention.
Figure 8B:
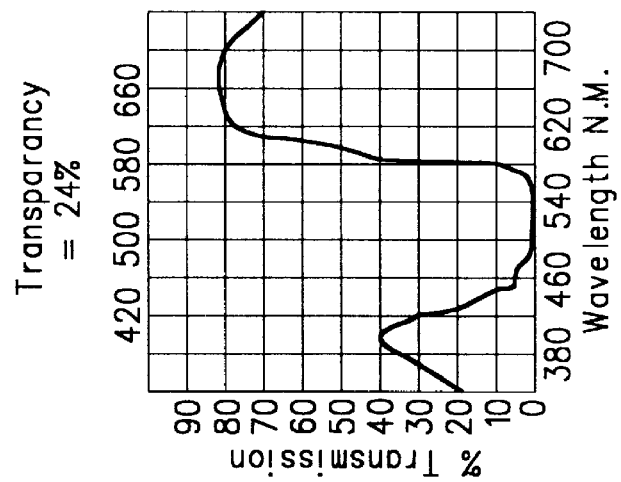
FIG. 8B is another graph of the percent of light transmission vs. the wavelength of light in nano-meters, illustrating the transparency or light wavelength characteristics of a preferred embodiment of the present Invention.
Figure 8A:
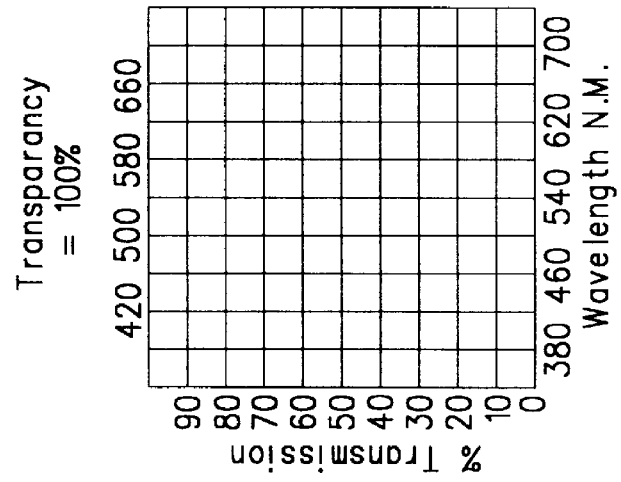
FIG. 8A is a graph of the percent of light transmission vs. the wavelength of light in nano-meters, illustrating the transparency or light wavelength characteristics of a preferred embodiment of the present Invention.

These Examination Test Slides 50, 55 and 60 may be produced as a single integrated component with the Test Area Section 30, or these slides may be inserted as a subcomponent to create a wholly integrated finished piece. In one preferred embodiment Examination Test Slides 50, 55 and 60 all have completely different light wave properties. For example, clear Test Slide 50 has a transparency factor equal to 100 percent as shown in FIG. 8A. Yellow Test Slide 55 has a transparency factor equal to 88 percent with associated wavelength properties as shown in FIG. 8C. Red Test Slide 60 has a transparency factor equal to 24 percent with associated wavelength properties as shown in FIG. 8B.

Certain UFI may only be seen under polarized light, therefore any or all Examination Test Slides 50, 55 and 60 could be made of a polarized plastic such as polycarbonate-like materials available from Polaroid Corporation of Massachusetts. Other UFI may not be visible or are harder to observe under ultraviolet light, therefore any or all Examination Test Slides 50, 55 and 60 could be made of polycarbonate-like materials which block ultraviolet light. In the alternative Examination Test Slides could have coatings applied which block the ultraviolet light spectrum. Such coatings or polycarbonate-like materials are readily known to those skilled in the art and are available from the previously mentioned Polaroid Corporation.

In the alternative, or in combination with the PFT Examination System and their associated Examination Test Slides 50, 55 and 60, natural light or artificial light with specific light wave properties may be employed. If the woman is using the PFT Examination System at night, artificial light will be required to perform PFT analysis. It is anticipated that the woman may use a battery powered flashlight specially dedicated or even tailored for use with the PFT. An individual light source offers the advantage of increasing the PFT Examination Systems independence, range of use and portability. It is contemplated that in other preferred embodiments such as an individual light source or sources may be integrated into the PFT Examination System. These embodiments are more fully delineated in these hereinafter entitled (6) Providing a Novel Battery Powered Microprocessor System to automatically perform the Positive Fertility Testing.

Other artificial lights may be used and include, but are not limited to, polarized light, ultraviolet light, coherent light such as a laser, incandescent light, florescent light, battery powered Light Emitting Diodes, coated lights, or lights equipped with specific kinds of filters, gels or acetates which change the light wave properties to the desired frequency. Certain types of dyes or stains may be employed on the surface of individual Examination Test Slides 50, 55 and 60 because they may also produce desirous changes of the light wave properties, thus making viewing easier. However, it is important that dyes or stains are selected which do not contaminate the female fluids or secretions being tested for Positive Fertility thereby modifying or invalidating the results of the PFT analysis. An important safety element is to construct the Test Area Section 30, and specifically the Examination Test Slides 50, 60, and 65 will not fracture or splinter since the PFT is being used next to the eye when viewing UFI and is also used orally to collect samples.

FIG. 3 shows a preferred embodiment where Examination Test Slide Retaining Ring 40 holds the Examination Test Slides 50, 55, and 60 in place. Examination Test Slide Retaining Ring 40 is constructed so that Examination Test Slides 50, 55 and 60 may be removed and replaced from Testing Section Area 30. This allows for used or damaged slides to be discarded and clean new slides to be inserted. An adhesive vinyl or plastic O-Ring 35 may also be used to firmly secure Examination Test Slide 50, 55 and 60 to Test Area Section 30. It is anticipated that slides may be used as an integrated light filter. These slides may also be removable giving great versatility to the user in making detailed UFI studies, comparisons or analyses.

Other embodiments relating to the use of specific wavelengths of light and of the PFT Examination System, especially relating to Examination Testing Slides, may include subsystems other than those specifically discussed or subsystems which can be included in place of, or in addition to, the subsystems described. Many such variations will be apparent to one skilled in the art.

(4) Compound Test Areas So That Multiple Positive Fertility Tests May Be Conducted Simultaneously In the preferred embodiment the present invention employs no chemicals, but rather light wave properties to interact with and perform Positive Fertility Testing. Multiple tests may be conducted in the integrated PFT Examination System without concern of chemical contamination. These multiple tests may be conducted on Examination Test Slides 50, 55 and 60 which use or embody different light wave properties to allow the user better visual readings or to observe different UFI interactions that may otherwise be invisible.

FIG. 9A shows that Fertile Phase 111 is extremely short with ovum survivability lasting only twelve to twenty-four hours. It is extremely critical for those trying to achieve pregnancy to be able to identify positive fertility and positive ovulation in order to optimize the chances of impregnation. A woman's choices were limited under the teachings of the prior art. Invariably the medical procedures and processes restricted the woman's activities to her home, or bed so that consistent time oriented tests could be performed. Daily visits to the hospital, and even hospitalization would be prescribed in order to determine positive ovulation in many instances. A woman may not always be near to, have access to, or the time or financial resources to use a clinic or hospital, or have the luxury or the time for a protracted bed rest period in favor of determining positive fertility. It is not unusual that the woman may have to work, or she may in fact be traveling away from her residence and in either circumstance, still have the need to resolve her fertility or reproductive health status.

The embodiment of an integrated compound test area in the PFT Examination System creates versatility, and economy. A woman may deposit the female fluid or secretion of her choice on Examination Test Slide 50 in the manner previously described or in a manner consistent with that of the art. She may immediately take another sample and place it on Examination Test Slide 55. Subsequently she may then take another sample and place it on Examination Test Slide 60. After the prepared PFT samples have been dried, UFI patterns may be observed. First, the user rotates the top triangle portion of the PFT Examination System Viewing Section 10 so that Microscope Bead Lens 15 is directly above and centered over Examination Test Slide 50. Second, the user looks through Microscope Bead Lens 15 in the manner previously described. Third, the user may note or record their UFI observations of the first PFT Sample. FIG. 9B gives an example of a chart that can be used for this purpose. Now the user rotates the top triangle portion of the PFT Examination System Viewing Section 10 so that Microscope Bead Lens 15 is directly above and centered over Examination Test Slide 55. The user looks through Microscope Bead Lens 15 in the manner previously described. The user may note or record their UFI observations of the second PFT Sample. Next the user rotates the top triangle portion of the PFT Examination System Viewing Section 10 so that Microscope Bead Lens 15 is directly above and centered over Examination Test Slide 60. The user then looks through Microscope Bead Lens 15 in the manner previously described. The user may note or record their UFI observations of the third PFT Sample. The use of Examination Test Slides 50, 55 and 60 which have different wavelength properties or in the alternative the use of light sources with different wavelength properties creates wide possibilities of combinations for cross comparison and observation of UFI on the three PFT samples collected.

A modification of the above procedure embodies a methodology for using multiple test slides to perform, what under the prior art are expensive and inconvenient a comparative staggered confirming fertility analysis. This example of multiple types of tests can be easily performed using the PFT Examination System and methodology. This particular PFT test can be utilized, among other things, to determine the precise moment of ovulation. Such a system may be desirous for those wishing to improve their opportunity for conception or in choosing the sex of their child as described more fully in Section (7) The PFT Examination System as Birth Control Device and a Tool for Reproductive Health.

In the preferred embodiment the user deposits and prepares the chosen female fluid or secretion on Examination Test Slide 50 in the manner previously described. Then the user Observes the UFI patterns on the PFT sample. The user may note or record the observed UFI pattern on a chart similar to the one in FIG. 9B. The user may then wait two hours and repeat the PFT analysis by collecting a second sample in the manner prescribed on Examination Test Slide 55. The user then observes the UFI patterns on the second PFT sample on Examination Test Slide 55. The user may record or note the observed UFI pattern. The user waits another two hours and repeats the PFT analysis by collecting a third sample on Examination Test Slide 60. The user observes the UFI patterns on the third PFT sample on Examination Test Slide 60. The user may record or note the observed UFI pattern. The PFT examination unit 30 may now be cleaned and reused to continue these staggered confirming tests.

There may be a desire to have the PFT samples reviewed by a third party. In this case the entire PFT Examination system may be conveyed or only the Test Area Section 30 may be provided to a third party, by detaching it from Viewing Section 10, as previously described. A new replacement Test Area Section 30 may be inserted into Viewing Section 10, thus reforming an integrated PFT Examination System. In this manner the staggered confirming test may continue as long as required. It should be noted that different time periods may be selected. The time periods described are merely illustrative and should not be construed to be limiting the embodiment. Many other types and kinds of multiple PFT analysis may be performed by those skilled in the art.

For many, the psychological pressure and stress associated with conception can be high and the need for an accurate testing methodology which the user controls is empowering and satisfies many other personal needs and requirements. By creating multiple test areas, the incidence of any possible misreading is reduced to negligible amounts as psychological comfort in Positive Fertility Testing increases. The embodiment of these compound test areas integrated in Test Area Section 30 achieves numerous other benefits and economies as further indicated.

(5) Performing Two Or More Positive Fertility Tests Simultaneously Using Different Female Fluids Or Secretions In the previous section (4) it was discussed how the embodiment of compound test areas integrated within Test Area Section 30 creates the opportunity to immediately perform various multiple confirming PFT tests using the same fluid or secretion. Another aspect of the preferred embodiment of the present Invention is implementing the ability to immediately perform two or more PFT analysis simultaneously. These simultaneous PFTs may be accomplished using different combinations of female fluids or secretions. This embodiment creates quantifiable and qualitative increases in accuracy and emphasizes the ability of the Invention to provide 100 percent precision if used as prescribed in determining time of ovulation thus providing additional psychological relief to the user.

In the preferred embodiment the Invention provides the woman with a choice of which fluids or secretions or combinations of fluids or secretions to use for Positive Fertility Testing. This is because UFI can be accurately observed in any female fluid or secretion correctly collected and prepared for PFT analysis. Those skilled in the art are familiar with the lancing of finger tips or the drawing of blood, in order to place a drop of blood or blood smear sample on any of the Examination Test Slides 50, 55 or 60. Urine can be collected on a swab or a probe or in a small cup then extracted with an eyedropper and deposited on an alternate remaining Examination Test Slide. Another fluid may be used for a third level comparison of UFI, or different PFT Examination Units or different Test Area Section 30s may be employed for the study and analysis of gynecological condition or reproductive health by professionals skilled in the art. Central Connecting Post 65 on Test Area 30 allows the detachment of Test Area Section 30 from the Viewing Section 10. A health practitioner or one skilled in the art can easily use the Test Area Section 30 and its integrated Examination Slides 50, 55 and 60 in combination with other laboratory equipment. This can include, but not be limited to, high powered laboratory scanning computer microscopes for more involved investigations or group studies and comparisons. Because the Examination Slides 50, 55 and 60 are removable, they may be stored or preserved for research purposes. The number of examination slides may be increased or decreased in other preferred embodiments and these slides may all have different light wavelength properties. For instance it is contemplated that a PFT Examination System with seven slides, one for every day of the week could be created.

Because there may be religious, personal convictions, prohibitions, misgivings, or health concerns against the use of blood or urine, other combinations of fluids may be used without violating the accuracy of the PFT analysis. The user may proceed with multiple tests with any of various combinations of different fluids. In the preferred embodiment saliva and cervical mucous are used. However, tears, breast milk, nasal mucous, vaginal transudate, etc. may be employed. Further embodiments of the Invention which include subsystems other than those specifically discussed can be included in place of, or in addition to, the subsystems described. Many such variations will be apparent to one of skill in the art.

Figure 7B:
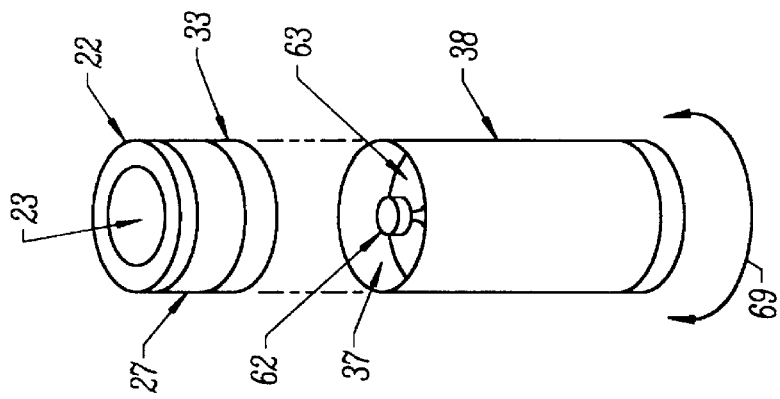
FIG. 7B shows a side view of another preferred embodiment of the present Invention using battery powered microprocessor devices.
Figure 7A:
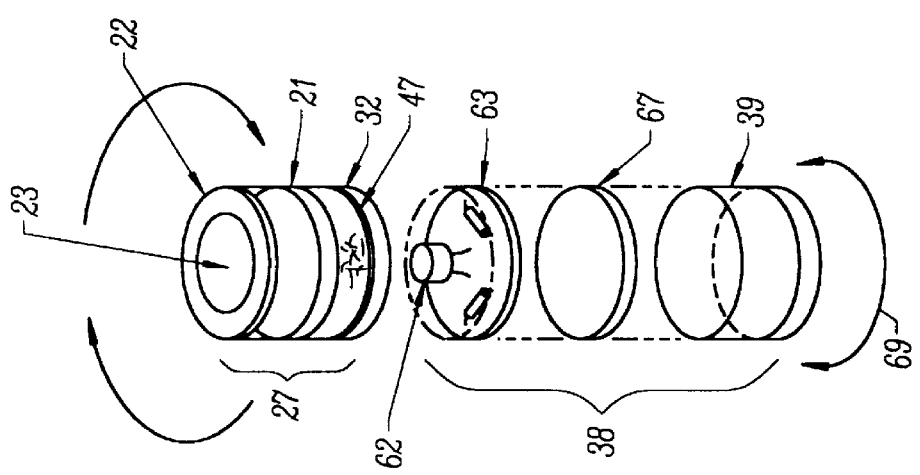
FIG. 7A shows an enlarged cross-section view of another preferred embodiment of the present Invention using battery powered microprocessor devices.

(6) Providing a Novel Battery Powered Microprocessor to automatically perform the Positive Fertility Testing FIGS. 7A and 7B show an alternate preferred embodiment of the PFT Examination System. In this embodiment the shape resembles a woman's lipstick case in size and outward appearance. This form is used for convenience and easy manipulation. However, the shape and any of the components or subcomponents described herein may be embodied in other form factors. The components or subcomponents described may be embodied collectively or independently depending on the desired purpose of use, cost considerations and other factors, thus providing maximum flexibility and versatility. There are three general areas of the PFT Examination System components to be considered in this section: (A) Alternative Lens System; (B) Independent Light Source; (C) Miniaturized Digital Camera with Computer Control Board and Memory System (A) Alternative Lens System. In FIG. 5B, Microscope Bead Lens 15, serves as a unique objective lens for the PFT Examination system. In FIGS. 7A and 7B Objective Lens 23 and Focusing Lens 21 have been substituted for Microscope Bead Lens 15. These lenses may be formed of optical glass or clear polycarbonate and fashioned by one skilled in the art to a lens system with a suitable focal length to provide clear fixed focus to Examination Test Slide 32 and affording a magnifying power suitable to clearly observe UFI patterns. Bevels, ridges or similar means on either or both Objective Lens Holder 22 or Lower Recessed Central Connecting Ring 33 provide fine focusing by rotating or pulling Objective 23 lens up or down PFT Viewing Tube Section 27. The joining of the PFT Viewing Tube 27 to the Lower Electronics Section 38 is accomplished by the joining of Lower Recessed Central Connecting Ring 33 which nestles into Coupling Connector Means 37. This joining allows PFT Viewing Tube Section 27 the ability to freely rotate 360 degrees, Rotation Angle 69, about Lower Electronics Section 38.

Female fluid or secretion, PFT Sample 47, is deposited and prepared on Examination Test Slide 32 in the manner previously described. Test Slide 32 may be formed of clear polycarbonate or similar material. Test Slide 32 is removable and may be subdivided into smaller component subsections each with different light wave properties as previously discussed in other sections. PFT Viewing Tube Section 27 is completely self-contained and may be used independent of Lower Electronics Section 38 for UFI observations. When PFT Viewing Tube 27 is integrated into Lower Electronics Section 38 as an operating base station many advantages and benefits are achieved as will be further indicated.

(B) Independent Light Source. The embodiment of Electronic Illumination Device 62 provides greater versatility and operating freedom for the user of the PFT Examination System. It allows the user to perform UFI pattern observations independent of time of day or the physical location. It is contemplated that Microprocessor Circuit Board 63 may hold several types of Electronic Illumination Device 62s or that the user may have several Lower Electronics Section 38s which have different functions and purposes unique to the research or investigation of UFI phenomena. Polarized, Ultraviolet and other wavelengths of light or their combinations may be directed into the PFT Viewing Tube Section 27 by Electronic Illumination Device(s) 62 for PFT sample preparation and UFI investigation and observation.

Microprocessor Circuit Board 63 controls and operates Electronic Illumination Device 62. It is also possible for one skilled in the art to arrange for Microprocessor Circuit Board 63 to be designed for different operating purposes and that the user can interchange them as desired.

Microprocessor Circuit Board 63 and Illumination Device 62 are powered from Battery 67. SR71A alkaline battery or similar, available from EverReady Corporation of St. Louis, Mo., has been found to be suitable for Battery 67 in a preferred embodiment. Electronics Control Section 39 provides access for battery replacement and houses the operating controls, including but not limited to, an ON/OFF switch, variable light intensity switch and an Operating Light Frequency Selection switch. Electronic Illumination Device(s) 62 may be an incandescent lamp bulb similar to 222BP-2 from EverReady Corporation; a Light Emitting Diode, "LED" similar to 5308H1 Superbrite LEDs or Bi-Color surface mount 6250F7LC both available from IDI Corporation of the United States, or a Neon Lamp similar to A2B(NE-2V) also available from IDI Corporation, or other similar battery powered illumination device known to one skilled in the art.

(C) Miniaturized Digital Camera with Computer Control Board and Memory System. With the advent of inexpensive, commercially available nano-technology, Microprocessor Circuit Board 63 may contain Random Access Memory circuits and include a Digital Camera 62. As previously stated, PFT Viewing Tube Section 27 may operate independent of Lower Electronics Section 38 for UFI observations. However, when PFT Viewing Tube 27 is integrated into Lower Electronics Section 38 it becomes an integrated PFT Examination System with computer assisted analysis capabilities. Intel Corporation of San Jose, Calif. are suitable suppliers of microprocessor and memory systems and Sharp Corporation of Tokyo, Japan has many subminiature digital cameras suitable for inclusion. Therefore, one skilled in the art has ready access to appropriate hardware and software interfaces to provide Microprocessor Circuit Board 63 and Electronics Control Section 39 the additional capability and capacity including, but not limited to: (i) The ability to store images of UFI for later observation or printing; (ii) The ability to automatically record and update a daily, monthly and yearly chart of a woman's fertility patterns and reproductive health status; (iii) The capability to provide for telecommunications to other third parties for digital transmission of UFI images for second opinions; (iv) The inclusion of an input/output interface means for downloading data to larger computer systems for UFI data base construction and comparison; (v) The ability to contain a data base image file of standard UFI patterns and include a pattern recognition algorithm for automatic UFI comparative analysis of PFT Samples; and (vi) An interface means so that digital images of UFI may be displayed on video display terminals or similar devices.

Further embodiments of the Invention which include subsystems other than those specifically discussed can be included in place of, or in addition to, the subsystems described. Many such variations will be apparent to one of skill in the art.

(7) The PFT Examination System as a Birth Control Device and a Tool for Reproductive Health In this preferred embodiment of the present Invention the processes to use PFT and the PFT Examination System as the most accurate indicator of positive ovulation is defined. Herein, are the procedures which a woman may pinpoint times of greatest fertility, thereby knowing the optimum time period for achieving pregnancy. In this manner four general concepts of PFT are explored: (A) The PFT Testing Methodology Associated With Increasing The Probability Of Having A Boy; (B) The PFT Testing Methodology Associated With Increasing The Probability Of Having A Girl; (C) The UFI Positive Pregnancy Sign, "PGS"; (D) The PFT Methodology Associated With Effective Birth Control.

(A) The PFT Testing Methodology Associated With Increasing The Probability Of Having A Boy Is As Follows. There are many different types of sperm cells. Some of the primary groups include, those which act as blockers, hunters, attackers, dissolvers and runners. While all spermatozoa theoretically may cause fertilization, the runner group is usually the predominate spermatozoa involved in fertilization. There are two primary types of runners, fast but weak and slow but strong, whose associated chromosomes produce male and female fertilized embryos respectively.

For those wishing to increase the probability of having a boy, intercourse with ejaculation or medically assisted implantation is withheld until positive ovulation signaled by FIG. 6B, Full Ferning 83 has occurred. To more precisely determine the moment of positive ovulation the user may perform the staggered confirming test methodology described in section (5) Performing Two or More PFTs Simultaneously Using Different Fluids or Secretions. The staggered confirming tests should be begun as soon as a UFI pattern similar to FIG. 6D, Beginning Ferning 85 occurs by itself or in conjunction with UFI pattern Canalization 87 of FIG. 6F. When a UFI pattern confirming ovulation has occurred, similar to Full Ferning 83, then intercourse with ejaculation or medically assisted implantation should commence. This procedure will assist the faster, but weaker male chromosome spermatozoa to reach the egg and successfully fertilize the ovum before their slower, but stronger female chromosome spermatozoa reach the egg.

(B) The PFT Testing Methodology Associated With Increasing The Probability Of Having A Girl Is As Follows. When a UFI pattern confirming late Canalization occurs, similar to FIG. 6F, Canalization 87, then intercourse with ejaculation or medically assisted implantation should commence. Intercourse with ejaculation or medically assisted implantation must be withheld after a UFI pattern similar to FIG. 6D, Beginning Ferning 85 occurs by itself or in conjunction with UFI pattern Canalization 87 of FIG. 6F. This procedure will assist the slower, but stronger female chromosome spermatozoa to reach the uterus and fallopian tubes and remain in place while the faster, but weaker male chromosome spermatozoa die off before the egg has been released. This will best facilitate the successful implantation and fertilization of the ovum with the female chromosome spermatozoa.

(C) The UFI Positive Pregnancy Sign, "PGS" From the moment of fertilization onward there are massive and profound changes of KFI in a woman's body. As would be expected, these KFI create new and different interactions.

From the point of fertilization until the birth of the baby KFI form new and specific electrochemical interdependencies which convey Universal Pregnancy Indices, "UPI." While testing for KFI during pregnancy presents unique challenges, limitations and problems, testing for UPI does not. Unlike KFI, UPI is testable regardless of concentration levels in all female fluids and secretions. UPI can be consistently tested for and uniformly interpreted with great accuracy for all pregnant women. PFT testing for UPI at once results in a remarkable simplification of the testing process during pregnancy and causes numerous benefits and economies.

Like UFI, UPI also may not be observed with the unaided eye. UPI may not be observed unless the sample has been collected and prepared in the same manner specified as that for UFI. When this is successfully accomplished then from any female fluid or secretion collected, it can be determined immediately by the tell-tale, visual reference pattern of these UPIs whether or not a woman is positively pregnant or not. In addition to her pregnancy status, the size and shapes of the patterns of UFI observed, crystals, fern, snow-flake, ice crystal, cubic, amorphous crystal, etc. provide tremendous amounts of information as to the immediate status of the pregnancy and gynecological condition of the woman. These UPI change over the course of the pregnancy in a similar or typically predictable pattern corresponding to the physiological changes within the woman and can be classified in groups of UPI associated with the first, second and third trimesters of pregnancy. Immediately after the birth of the child, there is another dramatic shift in the level KFI and a corresponding shift of UPI which marks the transitional boundary between UPI and the return of UFI.

Like UFI, these UPI have specific defined patterns which may be observed in the manner consistent with PFT and the use of the PFT Examination System. The first group of UPI which form the boundary between fertility and pregnancy are called Positive Pregnancy Signs, "PGS." PGS are highly distinctive, long crystalline patterns which do not diminish over time, but increase their definition and dimension over time. These PGS patterns are eventually replaced by other unique UPI patterns as the pregnancy progresses.

One skilled in the art can appreciate that there are numerous UPI and combinations of UPI patterns that are possible for the period of time from fertilization through the three trimesters of pregnancy up to childbirth. There are other patterns and interpretations of PFT indicative of the condition and status of the pregnancy and the woman's gynecological health during this time period as well. These can be readily determined and the utilized in different embodiments of PFT and PFT analysis of UPI by one skilled in the art without departing from the spirit of the Invention. For instance, by modifying the wavelength(s) of light entering Test Area Section 30 or Microscope Bead Lens 15, another preferred embodiment can be created to provide a PFT Examination System specifically tailored for analysis of UPI exclusively. Another preferred embodiment is a PFT and PFT Examination System specifically tailored for determining PGS exclusively. Combinations of PFT and PFT Examination Systems for the analysis of these UPI with UFI are also possible. Those discussed herein are merely illustrative and are by no means meant to limit the scope or application of the Invention.

(D) The PFT Methodology Associated with Effective Birth Control. As stated previously, the Fertile Phase 111 is of an extremely short duration. With ovum survivability of less than twenty-four hours the next most important fertilization factor to consider is spermatozoa survivability. The longest living sperm are the runners who are able to produce a girl. They appear to have a life span of approximately 72 hours. However, it is possible in the presence of a UFI pattern more pronounced than that of Full Ferning 83 that sperm life span can increase to up to five days. This is because the UFI associated with this pronounced ferning is physiologically seen in conjunction with a noticeable, significant increase of vaginal transudate and cervico-vaginal mucous. It is this type of uterine condition which can supply needed nutrients and a hospitable environment to increase the longevity of spermatozoa. Taking into account this type of condition, when a UFI pattern confirming late Canalization occurs, similar to FIG. 6F, Canalization 87, intercourse must be withheld. Otherwise, other contraceptive means must be utilized until after the ovum has ceased being viable. This is after the end of the Nurturing, Post Ovulatory phase 150. Intercourse with ejaculation should not commence until after all UFI signs of Broad Ferning 82 have vanished and UFI patterns indicating that the Premenstrual Phase 155 has commenced have been positively observed. This UFI signals the end of the Fertile Phase 111 and the beginning of the Infertile Period 122. It is appropriate to perform confirming PFT tests with different female fluids and secretions, as previously prescribed, to validate UFI observation of the Infertile Period 122. This procedure ensure that all spermatozoa have ceased being viable prior to egg release and that the ovum has ceased being viable prior to the reintroduction of spermatozoa. With this PFT process and procedure a woman can ensure to nearly 100% accuracy that pregnancy can be naturally and effectively postponed or avoided.

(8) Positive Male Fertility Testing Methodology, "PMFT" A Tool for Male Reproductive Health Male Universal Fertility Indices, "MUFI" are an observable phenomena using the PMFT Examination System. MUFI are the male equivalent of UFI and are a subset of the total observable UFI phenomenon. The embodiment of an accurate and immediate testing methodology to provide information as to the fertility status and reproductive health of a male is herein described. Issues of non-viable sperm, low sperm count, excessive testicular heat effect, impotence inducing factors, etc. can be effectively observed.

Like all female fluids and secretions, male fluids and secretions also convey key hormones, enzymes, salts, and other chemical carriers called Key Male Interactors, "KMI." Some KMI include, but are not limited to testosterone, glucose, electrolytes (sodium and potassium), salts and enzymes. KMI are present in all male fluids and secretions including saliva, sperm, semen, other ejaculatory fluids, blood, urine, and spinal fluid. The levels of individual KMI vary continually and indicate there exists a cycle for a man similar to that of a woman. These cycles are unique to each man and as can be anticipated, the levels of KMI are also distinct at any given moment in time. Prior art methods have focused on determinative testing to achieve interpretations of what the discreet levels of individual KMI may signify. Accumulating test samples of fluids which contain sufficient quantities of KMI for assay has been problematic as discussed. Keeping testing samples from perishing or free from contamination while under analysis has been equally challenging.

The present Invention offers a completely different approach. Rather than looking at individual KMI or combinations of KMI as the prior art teaches, the Invention formulates a new methodology, process and approach by examining the overall interactions which these KMI create among themselves. KMI form unique interactions with one another throughout the cycle of a man. However, these interactions are universal for all men. Therefore KMI form electrochemical interdependencies which convey Male Universal Fertility Indices, "MUFI" While KMI testing presents limitations and problems, testing for MUFI does not. Unlike KMI, MUFI is testable regardless of concentration levels in male fluids and secretions. MUFI can be consistently tested for and uniformly interpreted with great accuracy for all men. PFT testing for MUFI at once results in a remarkable simplification of the male fertility testing process and causes numerous benefits and economies.

MUFI may not be observed with the unaided eye. MUFI may not be observed unless the sample has been collected and prepared in the manner specified. When this is successfully accomplished then from any male fluid or secretion collected, it can be determined immediately by the tell-tale, visual reference pattern of these MUFIs the reproductive health and fertility status of a man. Additionally it is possible to directly view ejaculatory fluids and sperm to determine sperm count, viability and other fertility and health issues including identifying factors influencing or creating male sterility or impotence. The size and shapes of the patterns of MUFI observed, i.e. amorphous, canalized, randomized cells, noise, crystals, fern, snow-flake, etc. provide tremendous amounts of information as to the immediate reproductive health status of the man.

Like PFT there are three steps in Positive Male Fertility Testing. First is the collection and preparation of the sample (s). Second is the viewing of PMFT sample(s) under magnification and using the proper wavelength of light. And Third is the interpretation of the results of the PMFT which includes, but is not limited to, the recording and the comparison of prior PMFT results.

Figure 1A:
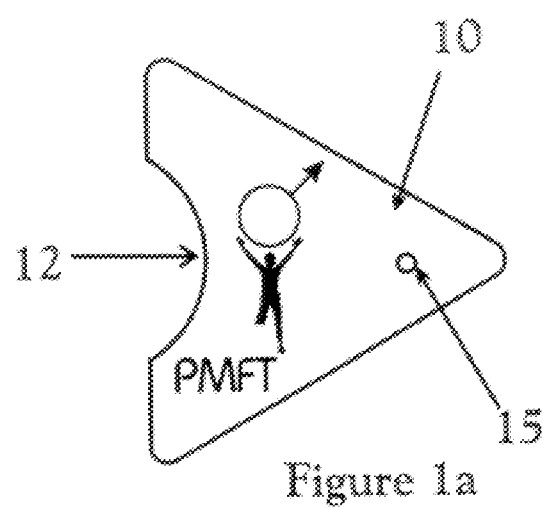
FIG. 1A shows a front view of another preferred embodiment of the present Invention displaying the Viewing Lens Section used for observing Male Universal Fertility Indices.

(A) The Collection of PMFT Sample(s). FIGS. 1A, 2, 3, SB and 5C show one example of a preferred embodiment of an integrated PMFT Examination System. The PMFT Examination System incorporates a small high powered microscope which allows the user to see the crystalline patterns of the MUFI. The PMFT Examination System is in the shape of a triangle with two disks that rotate from a center axis. FIGS. 1 and 2 show that Microscope Bead Lens 15 serves as the objective lens for the microscope and is housed in the upper disk Viewing Section 10. FIGS. 3 and 4 show that Test Area Section 30 serves as an integrated microscope stage, PMFT sample collecting and testing area and testing slide receptacle. In one preferred embodiment, Testing Area Section 30 Consists of three Examination Testing Slides, 50, 55 and 60 which are colored clear, yellow and red respectively. At least one of the Examination Slides, usually Test Slide 55, is fashioned with a recessed cavity as seen in FIG. 3 or Retaining Lip 35 so that a small sample of ejaculatory fluid, semen, etc. can be observed prior to drying to determine sperm count, sperm viability, and other tests and examinations known by one of skill in the art.

In one preferred embodiment, the Invention system uses a normally ejaculating man's semen or saliva to perform the PMFT analysis upon. Saliva is usually the easiest sample for a man to obtain. Begin with a PMFT Examination System which is sterile or clean. When saliva is used, it is recommended that the man analyzing his MUFI not eat or drink fluids 30 minutes prior to PMFT testing as this may dilute saliva and alter results. Often it is easier for a man to PMFT his semen or saliva at the beginning of the day before he has had anything to eat or drink.

Rotate the top triangle, Viewing Section 10, of the PMFT Examination System, so the clear Slide 50 on Testing Area Section 30 is easily accessible and facing the user. The user licks the top of clear Slide 50 so that it makes an even, thin film of saliva. Rotate the top triangle and lick the red Examination Test Slide 60. Next the user causes to be deposited a sample of ejaculatory fluid on yellow Examination Test Slide 55. First the user examines ejaculatory fluid PMFT sample on yellow Examination Test Slide 55. This should be accomplished by maintaining the PMFT Examination System in a horizontal position. The preferred embodiment includes an independent Illumination Means 62 as in FIG. 7A, which is powered by battery 67. A simple pressure contact switch on the PMFT Examination System provides ON/OFF and other control or light wavelength illumination capabilities. This facilitates viewing MUFIs on Examination Test Slides 50 and 60 as well as male fluid samples in a liquid state on Examination Test Slide 55. FIG. 6J shows Spermatozoa 250 in seminal fluid observed using PMFT Examination System.

Next Allow all the slides to dry completely. We recommend a natural drying process. However, the drying process may be accelerated, for instance, by placing the sample near a light bulb or in a place where the sun shines like a window sill.

If the man has any inflammation in his mouth or throat or if he drank liquids or ate food just before doing a test, it is recommended that ejaculatory fluid be substituted for saliva.

(B) The Viewing of the PMFT Sample(s). The MUFI crystal formations of the ejaculatory fluid tend to be more clearly identifiable. However, ejaculatory fluid readings may not be accurate if diluted or mixed with other fluids including those which are associated with intercourse or with condoms and other type of chemical contraceptives. Also, a sample which is too thick may be difficult to read. In cases of suspected infection, itching, inflammation, or changes in the characteristics of the fluid, use saliva or another male fluid or secretion such as tears, or urine.

In the preferred embodiment, the PMFT Examination System is a completely self-contained system and the visual result of the PMFT analysis may be obtained instantly. With the exception of view seminal or ejaculatory fluids for inspection and investigation in their liquid state, the accuracy of the PMFT analysis on MUFI does not degrade over a reasonable time if the man is unable to view the test immediately after the sample(s) have dried. A man may wish to have a doctor or other health practitioner view the slides for a second opinion. If desired, the Entire PMFT Examination system may be mailed or sent to a third party, or in the alternative FIG. 5B shows how Testing Area Section 30 may be detached from central connecting joint 25 so that only the Testing Area Section 30 need be supplied to a third party. A new, clean Testing Area Section 30 may be easily attached by inserting Central Connecting Post 65 into Self-Adjusting Microscope Lens Retaining Ring 20.

To view the PMFT sample(s) once they have dried, the user rotates the top triangle portion of the PMFT Examination System, Viewing Section 10, so that Microscope Bead Lens 15 is directly above and centered over Test Slide 50. Like UFI, some MUFI are not visible unless viewed under certain lighting conditions or using specific wavelengths of light. Using fluorescent, diffused light or direct sunlight may make it harder to see the results. For one skilled in the art embodiments tailored to particular light frequencies conducive to particular MUFI observation can be easily created. Examples of these type of PMFT Embodiments using other wavelengths of light are contained in the section entitled, (3) A Test Area Section With Replaceable Slides Where Different, Specific Wave Lengths of Light Are Employed.

While not required, it is suggested that a man choose a specific time every day, such as just after the man awakens, when PMFT testing can be consistently accomplished. In this way PMFT analysis can become a regular function of the morning, or daily routine.

(C) The Interpretation, Recording and Comparison of PMFT Results.

Because of KMI interactions in male fluids or secretions, some of which may occur upon drying of the sample, or the exposure of the PMFT to specific wavelengths of light, MUFI are revealed which delineate distinct and visible tell-tale patterns which may be viewed, interpreted, recorded and compared. The assessment of canalization and crystallization of MUFI in saliva, ejaculatory other male fluids and secretions and their variability has revealed a direct relationship with hormone levels and also with specific physiological states, conditions and circumstances.

These MUFI patterns revealed under PMFT include, but are not limited to those of FIGS. 6H Pointillism 230 and FIG. 6I Amorphic Crystals 240. The simplest PMFT analysis for ejaculatory fluid determines if the man's sperm cells are healthy and numerous. A PMFT semen analysis studies the quantity and quality of the man's spermatozoa. If the quantity of sperm cells is low, the man should wait at least 48 hours and perform the PMFT analysis again to determine if there is a physiological condition contributing to the condition. An infection may produce white blood cells in ejaculatory fluids. Additionally, antibodies may also be produced by a man to his own sperm cells. This may be especially true for men who have had vasectomies. A large number of dead spermatozoa may indicate sperm cell antibodies. A large number of deformed or unformed sperm cells, or sperm cells which are moving slowly or are non viable may indicate toxic environmental conditions, stress, exposure to toxic chemicals, improper diet or excessive testicular heat. Since spermatozoa require approximately 90 days to fully mature, PMFT analysis should reveal improved sperm cell condition within 90 days of the removal of the problem. A man can have a normal sex drive, erection and ejaculation while not having viable spermatozoa in his seminal fluid. Analysis of MUFI patterns may help to resolve whether this is due to reproductive organ damage.

Those couples whom have experienced fertility problems and wish to achieve pregnancy may find it is due to cervico-vaginal mucous and spermatozoa incompatibility by use of the PMFT. This phenomenon is due to the woman developing antibodies specific to her partner's sperm cells. CVF and spermatozoa compatibility may be tested utilizing the PMFT Examination system by depositing CVF mucous sample from the female onto PMFT Examination Slide 55 to which the male ejaculatory fluid is added. The user may observe the interaction to observe if incompatibility is the problem. PMFT analysis of the combined fluid's MUFI and UFI patterns may further resolve this issue.

Concluding Statement of the Preferred Embodiments In the foregoing specification, the Invention has been described with reference to specific exemplary embodiments. It will, however, be evident that various modifications and changes may be made without departing from the broader spirit and scope of the Invention as set forth in the appended claims. Many such changes or modifications will be readily apparent to one of ordinary skill in the art. The specification and drawings are, accordingly, to be regarded in an illustrative rather than a restrictive sense, the Invention being limited only by the provided claims.

We claim:

1. A device for diagnosing mammalian reproduction states utilizing mammalian fluids comprising;
    a. a testing area section including mammalian fluid sample containment means having at least a first fluid receptacle and a second fluid receptacle spaced along said testing area section from said first fluid holder;
    b. a viewing section having optical means for magnifying an image of said sample containment means; and
    c. means for selectively aligning said magnification means with said first and second fluid receptacles to observe the crystalline state of said fluid sample at said first and second fluid receptacles following evaporation of at least a portion of said fluid sample.

2. The device of claim 1 which further comprises means for removably supporting said first and second fluid receptacles to said testing area section.

3. The device of claim 1 in which said optical means comprises a borosilicate glass spheroid.

4. The device of claims 1 which additionally comprises illumination means for controlling light transmission through said first and second fluid receptacles.

5. The device of claims 4 in which said illumination means comprises forming said first and second fluid receptacles of a material capable of modifying light having wavelengths between 100 manometers and 2000 manometers.

6. The device of claim 5 which additionally comprises battery power means and a source of electromagnetic radiation to transmit electromagnetic radiation to said first and second receptacles.

7. The device of claim 1 which additionally comprises photographic means for obtaining images of said fluid sample following evaporation of at least a portion of said fluid sample from said first and second receptacles.

8. The device of claim 7 which additionally comprises memory means for storing said images obtained by said photographic means.

9. The device of claim 8 which additionally comprises means for retrieving said stored images.

10. The device of claim 1 in which said means for selectively aligning said magnification means with said first and second fluid receptacles, includes said testing area section and said viewing section being rotatable relative to one another to effect focusing of said optical means relative to said sample containment means.

11. The device of claim 10, in which said testing area section is a flexible body.

12. The device of claim 10 in which said viewing section is a flexible body.

* * * * *